United States Patent [19]

Murdock et al.

[11] Patent Number: 5,070,082

[45] Date of Patent: Dec. 3, 1991

[54] SOLUBILIZED PRO-DRUGS

[75] Inventors: Keith C. Murdock, Pearl River; Ving J. Lee, Monsey, both of N.Y.

[73] Assignee: American Cyanamid Company, Stamford, Conn.

[21] Appl. No.: 671,051

[22] Filed: Mar. 18, 1991

Related U.S. Application Data

[60] Division of Ser. No. 330,000, Mar. 31, 1989, abandoned, which is a continuation-in-part of Ser. No. 184,998, Apr. 22, 1988, abandoned, which is a continuation-in-part of Ser. No. 91,077, Aug. 31, 1987, abandoned, which is a continuation-in-part of Ser. No. 922,220, Oct. 23, 1986, abandoned.

[51] Int. Cl.⁵ .................. A61K 31/665; A61K 31/66; C07F 9/6574; C07F 9/24
[52] U.S. Cl. ..................... 514/105; 514/107; 514/118; 558/77; 558/84; 558/155; 558/157; 558/159; 562/10
[58] Field of Search .................. 558/157, 77, 84, 169; 562/10; 514/107, 118, 105

[56] References Cited

U.S. PATENT DOCUMENTS 2,394,003  2/1946  Newbery et al. .................. 562/112

*Primary Examiner*—Mary C. Lee
*Assistant Examiner*—Michael G. Ambrose
*Attorney, Agent, or Firm*—T. S. Szatkowski

[57] ABSTRACT

The N-phosphorylation of basic nitrogenous drug compounds to produce pro-drugs with enhanced water solubility or lipid solubility, or reduced toxicity, is disclosed. Drugs containing amine, amidine, guadinine, isourea, isothiourea an biguanide functions may be converted to such pro-drugs. The pro-drugs are hydrolyzed in the body, regenerating the original drugs with the release of a salt of phsophoric acid.

7 Claims, No Drawings

SOLUBILIZED PRO-DRUGS

This is a division of application Ser. No. 07/330,000, filed on Mar. 31, 1989, now abandoned, which is a continuation-in-part of Ser. No. 184,998, filed Apr. 22, 1988, now abandoned, which in turn is continuation-in-part of Ser. No. 091,077, filed Aug. 31, 1987, now abandoned, which in turn is a continuation-in-part of Ser. No. 922,220, filed Oct. 23, 1986, now abandoned.

BRIEF SUMMARY OF THE INVENTION

This invention is concerned with new organic compounds which are N-acylated derivatives of bis(2-imidazolin-2-ylhydrazones) of 9,10-anthracendicarboxaldehyde.

The unacylated precursor compounds are disclosed in U.S. Pat. No. 4,258,181, the contents and disclosure of which are hereby incorporated by reference.

Specifically this invention is concerned with compounds of the formula:

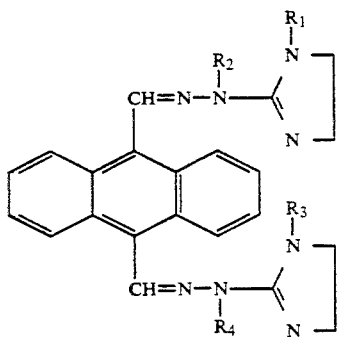

wherein $R_1$ and $R_3$ are the same or different and are: hydrogen, alkyl($C_1$-$C_6$),

((where $R_5$ is hydrogen, alkyl($C_1$-$C_6$), phenyl, monosubstituted phenyl (wherein the substituent may be ortho, meta or para and is fluoro, nitro, alkyl($C_1$-$C_6$), alkoxy($C_1$-$C_3$) or cyano), pentafluorophenyl, naphthyl, furanyl,

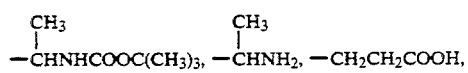

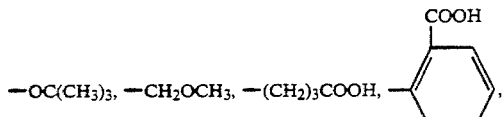

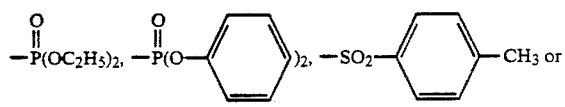

—$SO_3H$; and wherein only one of $R_1$ and $R_3$ may be hydrogen or alkyl($C_1$-$C_6$); $R_2$ and $R_4$ are the same or different and are: hydrogen, alkyl($C_1$-$C_4$) or

((where $R_6$ is hydrogen, alkyl($C_1$-$C_6$), phenyl, mono-substituted phenyl (wherein the substituent may be in the ortho, meta or para position and is fluoro, nitro, alkyl($C_1$-$C_6$), alkoxy($C_1$-$C_3$) or cyano), pentafluorophenyl, naphthyl, furanyl or —$CH_2OCH_3$)); together with the pharmacologically acceptable salts thereof.

Special mention is made of the monophosphoramidic acids embraced by the foregoing formula. Their antitumor activity is coupled with a lack of painful phlebitis near the site of injection when administered to some warm-blooded animals.

This invention is also directed to the preparation of N-phosphoryl pro-drugs for enhancing the water solubility or lipid solubility of a wide variety of nitrogenous drug compounds. In particular, the invention includes pro-drugs of the formula $B(Q)_n$ wherein B is the residue formed by removal of a hydrogen atom from one or more basic nitrogen atoms of an amine, amidine, guanidine, isourea, isothiourea or biguanide-containing pharmaceutically active compound for treating warm-blooded animals, Q is hydrogen or A, wherein A is

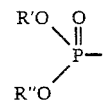

such that R' and R" may be the same or different and are R (where R is $C_1$-$C_6$ alkyl, aryl, aralkyl, heteroalkyl, NC—$CH_2CH_2$—,

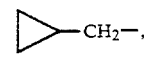

$Cl_3C$—$CH_2$— or $R_7OCH_2CH_2$—, where $R_7$ is hydrogen or $C_1$-$C_6$ alkyl), hydrogen, or a pharmaceutically acceptable cation or R' and R" are linked to form a —$CH_2CH_2$— or group, and n is an integer representing number of primary or secondary basic nitrogen atoms in the compound, such that at least one Q is A. Also included are the tautomerically shifted forms of such amidine, guanidine, isourea, isothiourea and biguanide residues.

DETAILED DESCRIPTION OF THE INVENTION

The compounds of the present invention are obtainable as yellow to orange crystalline materials having characteristic melting points and absorption spectra, and which may be purified by recrystallization from common organic solvents such as lower alkanols, dimethylformamide, methyl isobutyl ketone and the like.

The compounds of the present invention may be readily prepared in accordance with the following reaction scheme:

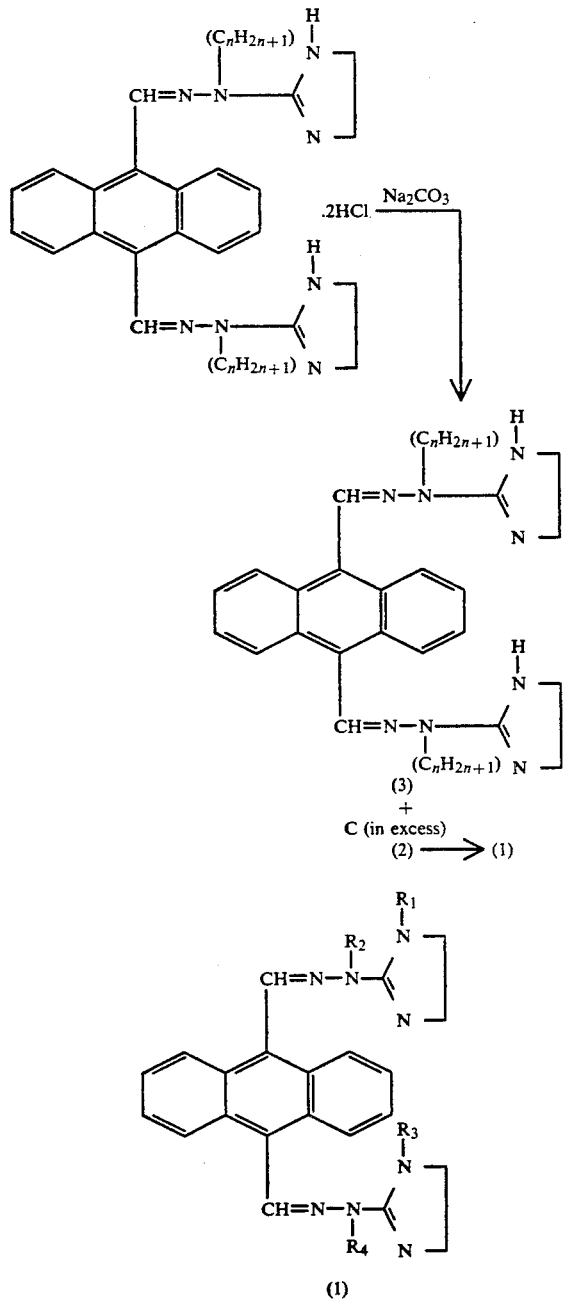

where C is an acylating agent including carboxylic acid anhydrides and acid chlorides, sulfonyl chlorides and the diester of a phosphoric acid chloride and where $R_1$, $R_2$, $R_3$ and $R_4$ are as hereinbefore defined.

An acylating anhydride may be employed without the need of an acid-binding agent. However, when acid chlorides are used in the acylation process, a non-basic acid-binding agent is employed to prevent major formation of the dihydrochloride of bis(2-imidazolin-2-ylhydrazone) of 9,10-anthracenedicarboxaldehyde as an undesired byproduct. A convenient non-basic acid-binding agent which is used for this purpose is N,O-bis(-trimethylsilyl) acetamide.

In accordance with the above reaction scheme, the dihydrochloride of bis(2-imidazolin-2-ylhydrazone) of 9,10-anthracenedicarboxaldehyde or an N,N'-dialkyl derivative (4), disclosed in U.S. Pat. No. 4,258,181, is treated with an aqueous solution of sodium carbonate and is allowed to stand for several hours to precipitate the free base compound (3). The product is collected by filtration, then dried in vacuo at about 110° C. for about 15 hours.

When the acylating agent C is an anhydride such as butyric anhydride, succinic anhydride, glutaric anhydride or 1,2-cyclohexane dicarboxylic anhydride and the like, the following procedure applies: The dried free base (3) is suspended and stirred in a dried solvent such as dichloromethane or N,N-dimethylformamide and the like, in an inert atmosphere, e.g., under nitrogen or argon and the like, then an excess of the anhydride (2) is added and stirring is continued until the solid is dissolved. The solution is allowed to stand at about 23° C. for 8–48 hours. The product (1) precipitates either spontaneously or after addition of ether or water, then is collected by filtration.

When the acylating agent (2) is an acid chloride such as benzoyl chloride, methoxyacetyl chloride, p-hexylbenzoyl chloride, m-nitrobenzoyl chloride, 2-furoyl chloride or diethyl chlorophosphate and the like, the following procedure is used: The dried bis(2-imidazolin-2-ylhydrazone) of 9,10-anthracenedicarboxaldeyde (3) is suspended and stirred in dichloromethane or the like, under argon or nitrogen in a closed round bottom flask equipped with a stirrer and a rubber septum cap, then an acid binding agent such as N,O-bis(trimethylsilyl)acetamide is added with stirring, using a weighed hypodermic syringe to inject the reagent through the rubber septum. Then the desired acid chloride is added in the same manner. The reaction mixture is stirred from three to sixty-four hours. The solution or suspension is chromatographed by dry column chromatography on alumina, and eluted with solvents such as dichloromethane, ethyl acetate, chloroform, acetone and the like. The cuts are collected and evaluated by thin layer chromatography on silica gel using solvent systems such as 3/1, 19/1 or 39/1 of chloroform/methanol, then the cuts containing the desired products are evaporated and purified by conventional means.

When, for example, the alkyl esters of mono and diphosphonic acid derivatives are to be converted to the corresponding free phosphonic acids, in an elegant modification according to this invention, a triarylphosphine, preferably triphenylphosphine will be used with the cleaving agent, e.g. iodotrialkylsilane, to remove byproduct alkyl iodide, thus precluding alkylation in other positions. This will be exemplified hereinafter.

Certain in vivo testing systems and protocols have been developed by the National Cancer Institute for testing compounds to determine their suitability as antineoplastic agents. These have been reported in "Cancer Chemotherapy Reports", Part III, Vol. 3, No. 2 (1972), by Deran, Greenberg, MacDonald, Schumacher and Abbott. These protocols have established standardized screening tests which are generally followed in the field of testing for antitumor agents. Three of these systems are particularly significant to the present invention. They are lymphocytic leukemia P388, melanotic melanoma B16 and lymphocytic leukemia L1210. All of these neoplasms grow in mice. Generally, good antitumor activity, shown in these protocols by a percentage increase of mean survival times of the treated (T) animals over the control (C) animals, is predictive of similar results in human leukemias.

Lymphocytic leukemia P388 test

The animals used were BDF1 mice all of one sex per test, weighing a minimum of 17 g and all within a 3 g weight range per test. There were 6 animals per test group. The tumor transplant was by intraperitoneal injection of 0.5 ml of diluted ascitic fluid containing $10^6$ cells of lymphocytic leukemia P388. The test compounds were administered intraperitoneally on days 1, 5 and 9 (relative to tumor inoculation) at various doses. The animals were weighed and survivors recorded on a regular basis for 60 days. The median survival time and the ratios for treated (T)/control (C) animals were calculated. The positive control compound was either 5-fluorouracil, given as a 60 mg/kg injection, or bis(2-imidazolin-2-ylhydrazone) of 9,10-anthracenedicarboxaldehyde dihydrochloride hereinafter called positive control A or B, respectively given as a 25 mg/kg injection. The results of this test with representative compounds of the present invention appear in Table I.

TABLE I

| Lymphocytic Leukemia P388 Test | | | |
|---|---|---|---|
| Compound | Dose (mg/kg) | Median Survival (Days) | T/C × 100 % |
| 2-[[10-[[Acetyl(1-acetyl-4,5-dihydro-1H-imidazol-2-yl)hydrazono]methyl]-9-anthracenyl]methylene]-1-(4,5-dihydro-1H-imidazol-2-yl)hydrazide of acetic acid | 200 | 17.5 | 175 |
| | 100 | 17 | 170 |
| | 50 | 16.5 | 165 |
| | 25 | 15.5 | 155 |
| | 12.5 | 13 | 130 |
| | 6.25 | 12.5 | 125 |
| Control | — | 10 | — |
| Positive Control B | 25 | 21.5 | 215 |
| 2,2'-[9,10-Anthracenediylbis(methylidyne-1-hydrazinyl-2-ylidene)] bis[4,5-dihydro-1-(1-oxobutyl)-1H-imidazole | 200 | 15.5 | 155 |
| | 100 | 14.5 | 145 |
| | 50 | 14 | 140 |
| | 25 | 12.5 | 125 |
| | 12.5 | 12.5 | 125 |
| Control | — | 10 | — |
| Positive Control B | 25 | 21.5 | 215 |
| 2,2'-[9,10-Anthracenediylbis(methylidyne-1-hydrazinyl-2-ylidene)]-bis[4,5-dihydro-gamma-oxo-1H-imidazole-1-butanoic acid] | 12.5 | 23 | 230 |
| | 6.25 | 19 | 190 |
| | 3.12 | 19 | 190 |
| | 1.56 | 17 | 170 |
| | 0.78 | 17 | 170 |
| | 0.39 | 15.5 | 155 |
| | 0.19 | 15 | 150 |
| Control | — | 10 | — |
| Positive Control A | 60 | 17.5 | 175 |
| 9,10-Anthracenediylbis[methylidyne-1-hydrazinyl-2-ylidene(4,5-dihydro-1H-imidazol-2,1-diyl)]]bisphosphonic acid, tetraphenyl ester | 200 | 16 | 160 |
| | 100 | 15.5 | 155 |
| | 50 | 13 | 130 |
| Control | — | 10 | — |
| Positive Control A | 60 | 17.5 | 175 |
| 9,10-Anthracenediylbis[methylidyne-1-hydrazinyl-2-ylidene(4,5-dihydro-1H-imidazole-2,1-diyl)]]bisphosphonic acid, tetraethyl ester | 100 | 12 | 120 |
| Control | — | 10 | 0 |
| Positive Control A | 60 | 17.5 | 175 |
| 9,10-Anthracenediylbis[methylidyne-1-hydrazinyl-2-ylidene(4,5-dihydro-1H-imidazole-2,1-diyl)]]bisphosphonic acid | 25 | 36.5 | 365 |
| | 12.5 | 27.5 | 275 |
| | 6.25 | 22 | 220 |
| | 3.12 | 18 | 180 |
| | 1.56 | 17 | 170 |
| | 0.78 | 17.5 | 175 |
| Control | — | 10 | — |
| Positive Control A | 60 | 17.5 | 175 |
| 2,2'-(9,10-Anthracene- | 200 | 32 | 320 |

TABLE I-continued

| Lymphocytic Leukemia P388 Test | | | |
|---|---|---|---|
| Compound | Dose (mg/kg) | Median Survival (Days) | T/C × 100 % |
| diyldimethylidyne)bis-[1-(1-benzoyl-4,5-dihydro 1H-imidazol-2-yl)hydrazide] of benzoic acid | 100 | 23 | 320 |
| | 50 | 20 | 200 |
| | 25 | 19.5 | 195 |
| | 12.5 | 19 | 190 |
| | 6.25 | 18 | 180 |
| | 3.12 | 17 | 170 |
| | 1.56 | 17.5 | 175 |
| | 0.78 | 15.5 | 155 |
| Control | — | 10 | — |
| Positive Control A | 60 | 23 | 230 |
| 2,2'-9,10-Anthracenediyldimethylidyne)bis[1-[4,5-dihydro-1-(methoxyacetyl)-1H-imidazol-2-yl]hydrazide] of methoxyacetic acid | 200 | 16.5 | 150 |
| | 50 | 16.5 | 150 |
| | 12.5 | 16.5 | 150 |
| | 3.12 | 14.5 | 132 |
| Control | — | 11 | — |
| Positive Control B | 25 | 32.5 | 295 |
| 2,2'-[9,10-Anthracenediylbis(methylidyne-1-hydrazinyl-2-ylidene)]bis [4,5-dihydro-delta-oxo-1H-imidazole-1-pentanoic acid] | 200 | 23 | 209 |
| | 50 | 19 | 173 |
| | 12.5 | 18 | 164 |
| | 3.12 | 15.5 | 141 |
| Control | — | 11 | — |
| Positive Control B | 25 | 32.5 | 295 |
| 2,2'-[9,10-Anthracenediylbis(methylidyne-1-hydrazinyl-2-ylidene)] bis[4,5-dihydro-1-[(4-methylphenyl)sulfonyl]-1H-imidazole] | 200 | 14 | 127 |
| | 50 | 14 | 127 |
| Control | — | 11 | — |
| Positive Control A | 25 | 32.5 | 295 |
| 2,2'-(9,10-Anthracenediyldimethylidyne)bis[1-[1-(4-hexylbenzoyl)-4,5-dihydro-1H-imidazol-2-yl]hydrazide] of 4-hexylbenzoic acid | 200 | 14 | 127 |
| Control | — | 11 | — |
| Positive Control A | 60 | 20 | 182 |
| 2,2'-(Anthracenediyldimethylidyne)bis[1-[4,5-dihydro-1-(3-nitrobenzoyl)-1H-imidazol-2-yl]hydrazide] of 3-nitrobenzoic acid | 200 | 21.5 | 179 |
| | 100 | 18 | 150 |
| | 50 | 16.5 | 138 |
| | 25 | 18 | 150 |
| | 12.5 | 13.5 | 113 |
| | 6.25 | 16 | 133 |
| | 3.12 | 16 | 133 |
| Control | — | 12 | — |
| Positive Control A | 60 | 21.5 | 179 |
| 2,2'-(9,10-Anthracenediyldimethylidene)bis[1-[4,5-dihydro-1-(4-methoxybenzoyl)-1H-imidazol-2-yl]hydrazide] of 4-methoxybenzoic acid | 200 | 16 | 139 |
| Control | — | 11.5 | — |
| Positive Control B | 25 | 16 | 139 |
| 2,2'-[9,10-Anthracenediylbis(methylidyne-1-hydrazinyl-2-ylidene)] bis[4,5-dihydro-1H-imidazole-1-carboxylic acid], bis(1,1-dimethylethyl) ester | 50 | 31.5 | 274 |
| | 25 | 22 | 191 |
| | 12.25 | 17.5 | 152 |
| Control | — | 11.5 | — |
| Positive Control B | 25 | 16 | 139 |
| 2,2-(Anthracenediyldimethylidyne)bis[1-[1-(2-furanylcarbonyl)-4,5-dihydro-1H-imidazol-2-yl]hydrazide] of 2-furancarboxylic acid | 200 | 12 | 120 |
| Control | — | 10 | — |
| Positive Control A | 60 | 17 | 170 |
| 2,2'-[9,10-Anthracene- | 200 | 12 | 120 |

TABLE I-continued

Lymphocytic Leukemia P388 Test

| Compound | Dose (mg/kg) | Median Survival (Days) | T/C × 100 % |
|---|---|---|---|
| diylbis(methylidyne-1-hydrazinyl-2-ylidene)bis[4,5-dihydro]-1H-imidazol-1-carboxaldehyde] | 50 | 12 | 120 |
| Control | — | 10 | — |
| Positive Control A | 60 | 17 | 170 |
| 2,2'-[9,10-Anthracene-diylbis[methylidyne-1-hydrazinyl-2-ylidene(4,5-dihydro-1H-imidazole-2,1-diyl)carbonyl]]biscyclohexanecarboxylic acid | 25 | 18 | 164 |
|  | 12.5 | 16 | 145 |
|  | 6.25 | 13.5 | 123 |
| Control | — | 11 | — |
| Positive Control B | 25 | 33 | 300 |
| 2,2'-(9,10-Anthracene-diyldimethylidyne)bis[1-[1-(3,3-dimethyl-1-oxobutyl)-4,5-dihydro-1H-imidazol-2-yl]hydrazide] of 3,3-dimethyl butanoic acid | 200 | 13 | 118 |
|  | 100 | 12 | 109 |
| Control | — | 11 | — |
| Positive Control A | 60 | 20 | 182 |
| 2,2'-(9,10-Anthracene-diyldimethylidyne)bis[1-[4,5-dihydro-1-(1-oxobutyl)-1H-imidazol-2-yl]hydrazide] of butanoic acid | 200 | 11.5 | 105 |
| Control | — | 11 | — |
| Positive Control B | 25 | 32.5 | 295 |
| 2,2'-[9,10-Anthracene-diylbis(methylidyne-1-hydrazinyl-2-ylidene)]bis[1-acetyl-4,5-dihydro-1H-imidazole] | 50 | 11 | 110 |
|  | 25 | 10.5 | 105 |
|  | 12.5 | 10.5 | 105 |
|  | 6.25 | 10.5 | 105 |
| Control | — | 10 | — |
| Positive Control A | 60 | 11.5 | 115 |
| 2,2'-(9,10-Anthracene-diyldimethylidyne)bis[1-(1-acetyl-4,5-dihydro-1H-imidazol-2-yl)hydrazide] of acetic acid | 100 | 11 | 110 |
|  | 50 | 10.5 | 105 |
|  | 12.5 | 10.5 | 105 |
| Control | — | 101 | — |
| Positive Control A | 60 | 23 | 230 |
| 2,2'-(9,10-Anthracene-diyldimethylidyne)bis[1-[1-(2-fluorobenzoyl)-4,5-dihydro-1H-imidazol-2-yl]hydrazide] of 2-fluorobenzoic acid | 200 | 12 | 109 |
|  | 100 | 13 | 118 |
|  | 50 | 13 | 118 |
|  | 25 | 12 | 109 |
| Control | — | 11 | — |
| Positive Control A | 60 | 20 | 182 |
| 2,2'-[9,10-Anthracene-diylbis[methylidyne(1-formyl-1-hydrazinyl-2-ylidene)]]bis-[4,5-dihydro-1H-imidazole-1-carboxaldehyde] | 200 | 11.5 | 115 |
|  | 50 | 11 | 110 |
|  | 12.5 | 10.5 | 105 |
| Control | — | 10 | — |
| Positive Control A | 60 | 17 | 170 |
| 2,2'-(9,10-Anthracene-diyldimethylidyne)bis[1-[4,5-dihydro-1-(2-naphthalenylcarbonyl)-1H-imidazol-2-yl]hydrazide] of 2-naphthoic acid | 100 | 12 | 104 |
| Control | — | 11.5 | — |
| Positive Control B | 12.5 | 19 | 165 |
| 2,2'-(9,10-Anthracene-diyldimethylidyne)bis-[1-[1-(4-cyanobenzoyl)-4,5-dihydro-1H-imidazol-2-yl]hydrazide] of 4-cyanobenzoic acid | 200 | 14.5 | 132 |
|  | 100 | 14.5 | 132 |
|  | 50 | 12.5 | 114 |
|  | 25 | 12 | 109 |
| Control | — | 11 | — |
| Positive Control A | 60 | 20 | 182 |
| 2,2'-(9,10-Anthracene-diyldimethylidyne)bis[1-[4,5-dihydro-1-(pentafluoro-1H-imidazol-2-yl]hydrazide] of pentafluorobenzoic acid | 200 | 12 | 109 |
| Control | — | 11 | — |
| Positive Control A | 60 | 20 | 182 |
| [2-[[[10-[[4,5-dihydro-1H-imidazol-2-ylethyl-hydrazono]methyl]-9-anthracenyl]methylene]-hydrazino]-4,5-dihydro-1H-imidazol-1-yl]phosphonic acid, hydroiodide | 50 | 25.5 | 232 |
|  | 25 | 25 | 227 |
|  | 12.5 | 25 | 227 |
|  | 6.3 | 24 | 218 |
|  | 3.2 | 22.5 | 205 |
|  | 1.6 | 18 | 164 |
|  | 0.8 | 21.5 | 195 |
|  | 0.4 | 18 | 164 |
| Control | — | 11 | — |
| Positive Control A | 60 | 22 | 200 |
| [2[[[10-[[4,5-dihydro-1H-imidazol-2-yl)hydrazono]methyl]9-anthracenyl]methylene]hydrazino]-4,5-dihydro-1H-imidazol-1-yl]phosphonic acid, hydroiodide | 25 | >60 | >545 |
|  | 12.5 | 53.5 | 486 |
|  | 6.3 | 22 | 200 |
|  | 3.2 | 24 | 218 |
|  | 1.6 | 24.5 | 223 |
|  | 0.8 | 19 | 173 |
|  | 0.4 | 21 | 191 |
| Control | — | 11 | — |
| Positive Control A | 60 | 22 | 200 |
| [2-[[[10-[[4,5-dihydro-1H-imidazol-2-yl)hydrazono]methyl]-9-anthracenyl]methylene]hydrazino]-4,5-dihydro-1H-imidazol-1-yl]phosphonic acid, diethyl ester | 100 | 47 | 427 |
|  | 50 | 49 | 445 |
|  | 25 | 44.5 | 405 |
|  | 12.5 | 19 | 173 |
|  | 6.3 | 21.5 | 195 |
|  | 3.2 | 23.5 | 214 |
|  | 1.6 | 22.5 | 205 |
|  | 0.8 | 19 | 173 |
|  | 0.4 | 18 | 164 |
| Control | — | 11 | — |
| Positive Control A | 60 | 22 | 200 |

Melanotic Melanoma B16

The animals used were BDF1 mice, all of one sex, weighing a minimum of 17 g, and all within a 3 g weight range. There were normally 12 animals per test group, and 18 animals per control group. A one gram portion of melanotic melanoma B16 tumor was homogenized in 10 ml of Eagle's Minimum Essential Medium, supplemented with 2% fetal calf serum, and a 0.5 ml aliquot of the homogenate was implanted intraperitoneally into each test mouse. The test compounds were administered intraperitoneally on days 1, 5 and 9 (relative to tumor inoculation) at various doses. The animals were weighed and survivors recorded on a regular basis for 60 days. The median survival time and the ratio of survival time for treated (T)/control (C) animals were calculated. The positive control compound was bis(2-imidazolin-2ylhydrazone) of 9,10-anthracenedicarboxaldehyde dihydrochloride (hereinafter called positive control) given as intraperitoneal injection at a dose of 25 mg/kg on days 1, 5 and 9 (relative to tumor inoculation). The results of this test with representative compounds of the present invention appear in Table II.

TABLE II

Melanotic Melanoma B16 Test

| Compound | Dose (mg/kg) | Median Survival (Days) | T/C × 100 % |
|---|---|---|---|
| 2,2'-(9,10-Anthracene- | 12.5 | 55.5 | 252 |

TABLE II-continued

Melanotic Melanoma B16 Test

| Compound | Dose (mg/kg) | Survival (Days) | Median T/C × 100 % |
|---|---|---|---|
| diylbis(methylidyne-1- | 6.25 | >60 | >273 |
| hydrazinyl-2-ylidene)]- | 3.25 | >60 | >273 |
| bis[4,5-dihydro-gamma | | | |
| oxo-1H-imidazole-1- | | | |
| butanoic acid] | | | |
| Control | — | 22 | — |
| Positive Control B | 25 | 27 | 123 |
| [9,10-Anthracenediylbis- | 25 | 37.5 | 163 |
| [methylidyne-1-hydra- | 6.25 | 35.5 | 154 |
| zinyl-2-ylidene(4,5-di- | 1.56 | 29 | 126 |
| hydro-1H-imidazole-2,1- | | | |
| diyl)]]bisphosphonic | | | |
| acid | | | |
| Control | — | 23 | — |
| Positive Control B | 25 | 53 | 230 |
| 2,2'-(9,10-Anthracenediyl- | 200 | 50 | 227 |
| dimethylidyne)bis[1-(1- | 100 | 57.5 | 261 |
| benzoyl-4,5-dihydro-1H- | 50 | 40 | 182 |
| imidazol-2-yl)hydrazide] | 25 | 32 | 145 |
| of benzoic acid | 12.5 | 29.5 | 134 |
| Control | — | 22 | — |
| Positive Control B | 25 | 57.5 | 261 |
| | 12.5 | >60 | >273 |
| 2-[[10-[[Acetyl(1-ace- | 200 | 40 | 182 |
| tyl-4,5-dihydro-1H- | 100 | 37 | 168 |
| imidazol-2-yl)-hydra- | 50 | 29.5 | 134 |
| zono]methyl]-9-anthracenyl]- | 25 | 30 | 136 |
| methylene]-1-(4,5-dihydro- | 12.5 | 28 | 127 |
| 1H-imidazol-2-yl)-hydrazide | | | |
| of acetic acid. | | | |
| Control | — | 22 | — |
| Positive Control B | 25 | 57.5 | 261 |
| | 12.5 | >60 | >273 |
| 2,2'-[9,10-Anthracene- | 200 | 27.5 | 125 |
| diylbis(methylidyne-1- | 100 | 28.5 | 130 |
| hydrazinyl-2-ylidene)]- | 50 | 24.5 | 111 |
| bis[4,5-dihydro-1-(1- | 25 | 26 | 118 |
| oxobutyl)-1H-imidazole] | | | |
| Control | — | 22 | — |
| Positive Control B | 25 | 57.5 | 261 |
| | 12.5 | >60 | >273 |

Lymphocytic Leukemia L1210 Test

The animals used were BDF1 mice, all of one sex, weighing a minimum of 17 g and all within a 3 g weight range. There were 6 mice per test group and 18 in control groups. The tumor transplant was by intraperitoneal injection of 0.5 ml of diluted ascites containing $10^5$ viable L1210 leukemia cells per mouse. The test compounds were administered intraperitoneally on days 1, 5 and 9 (relative to tumor inoculation) at various doses. The animals were weighed and survivors recorded on a regular basis for 30 days. The mean survival time and the ratio of survival time for treated (T)/control(C) animals were calculated. The positive control compound was 5-fluorouracil given intraperitoneally at 60 mg/kg. The results of this test appear in Table III.

TABLE III

Lymphocytic Leukemia L1210 Test

| Compound | Dose (mg/kg) | Median Survival (Days) | T/C × 100 % |
|---|---|---|---|
| 2,2'-[9,10-Anthracene- | 12.5 | 13.2 | 155 |
| diylbis(methylidyne-1- | 6.25 | 12.2 | 144 |
| hydrazinyl-2-ylidene)]- | 3.12 | 12.3 | 145 |
| bis[4,5-dihydro-gamma- | 1.56 | 12 | 141 |
| oxo-1H-imidazole-1- | 0.78 | 11.2 | 132 |
| butanoic acid] | 0.39 | 11.5 | 135 |
| Control | — | 8.5 | — |
| 5-Fluorouracil A | 60 | 16.8 | 198 |

TABLE III-continued

Lymphocytic Leukemia L1210 Test

| Compound | Dose (mg/kg) | Median Survival (Days) | T/C × 100 % |
|---|---|---|---|
| [9,10-Anthracenediyl- | 25 | 17 | 200 |
| bis[methylidyne-1-hydra- | 12.5 | 13.3 | 156 |
| zinyl-2-ylidene(4,5- | 6.25 | 13.2 | 155 |
| dihydro-1H-imidazole-2, | 3.12 | 12.2 | 144 |
| 1-diyl)]]bisphosphonic | 1.56 | 11.5 | 135 |
| acid | 0.78 | 10.7 | 126 |
| Control | — | 8.5 | — |
| Positive Control A | 60 | 16.8 | 198 |

Also embraced within the purview of the present invention are therapeutic compositions of matter useful for ameliorating cancer diseases in mammals which contain the acylation products of the present invention as the active ingredients thereof.

This aspect of the invention includes the compositions of matter and the method of inducing the regression and/or palliation of leukemia and related cancers in mammals when administered in amounts ranging from about 0.075 mg to about 300 mg per square meter of mammalian body surface area per day. The interelationship of dosages for animals of various sizes and species and humans (based on mg/m² of surface area) is described by Freireich, E. J., et al., Quantitative Comparison of Toxicity of Anticancer Agents in Mouse, Rat, Hamster, Dog, Monkey, and Man, Cancer Chemother. Rep., 50, No. 4, 219-244, May, 1966. A preferred dosage regimen for optimum results would be from about 3.0 mg/m²/day to about 150 mg/m²/day. Such dosage units are employed that a total of from about 0.5 mg to about 525 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage, and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptabale carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg, with from about 10 to about 500 mg being preferred. Expressed in proportions, the active compound is generally present in from about 0.1 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administrated. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic natue to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

The clinical use of some anti-tumor agents, particularly anthracene derivatives, has been reported to be accompanied by a painful phlebitis in some patients near the site of injection. This phlebitis appears to be associated with the precipitation of the free base of the agent within the blood vessel due to basification of its acid addition salts e.g., the hydrochloride salt, by the blood.

It has now been discovered that the di- and the monophosphoramidic acid derivatives of the antitumor compound, bisantrene, provided by this invention exhibit excellent efficacy without the attendant phlebitis—precipitation problems seen in the prior art. Both of these derivatives exist as soluble anionic salts at physiological pH, i.e., 7.4. This enhanced solubility apparently reduces if not eliminates altogether any phlebitis reaction near the site of injection. As will be described in the following section, no precipitation of the monophosphoramidic acid compound is detected in a rat tail-vein model.

In the rat, the diphosphoramidic compound was found to be a pro-drug for bisantrene. The diphosphoramidic compound hydrolyzes rapidly to an intermediate form, the monophosphoramidic acid, and this, in turn, slowly hydrolyzes further to bisantrene after distribution of the drug throughout the animal. These in vivo hydrolyses are apparently enzymatic because the diphosphoramidic compound has been shown to be much more stable in water. Furthermore, the stability in water is more than adequate for an efficient formulation via lyophilization.

In a further aspect of this invention, mono- and diphosphoramidic acid derivatives of a wide variety of primary and secondary nitrogenous drug compounds may be prepared. These phosphoramidic mono- and diesters also function as pro-drugs by improving the solubility of the drugs in bodily fluids, as will now be described.

Poor solubility of drugs within warm-blooded animal patients is a substantial problem. It can be especially troublesome with certain amines, amidines, guanidines, isoureas, isothioureas and biguanides, which are poorly soluble in water as their free bases. These bases can often be solubilized in water as salts with various acids, but these give solutions which are usually acidic. Injectable formulations of these acidic solutions can lead to precipitation of the fully or partially neutralized bases near the site of injection as their acidic salts are basified by the buffering action of blood, lymph or other body fluids. Such precipitation can lead to inflammation, pain, phlebitis or other adverse reactions near the site of injection and limit the dosage to suboptimal levels. Extravasation (missing the vein) with a drug such as the antitumor agent doxorubicin can cause damaging focal necroses which are very slow to heal.

Clinically effective drugs with basic nitrogen atoms known to cause phlebitis include ceftizoxime and related antibiotics in the cephalosporin and penicillin families, ciprofloxacin and other quinolone antibiotics, bisantrene and amsacrine (antitumor agents).

Other basic drugs with poor aqueous solubility at neutrality are still in the experimental stage (Z=H):

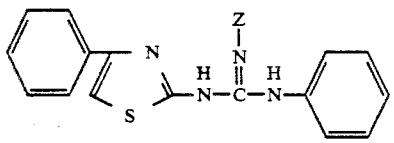
A

The compound A, [1-(4-Phenyl-2-thiazolyl)-3-phenyl-guanidine)], is active against rhinoviruses and is disclosed in commonly-assigned U.S. Pat. No. 4,089,965, which is incorporated by reference.

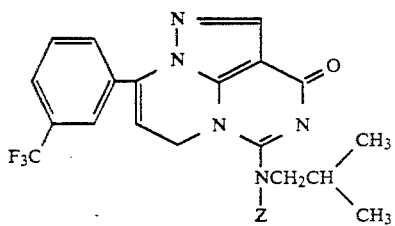
B

The compound B, [5-(2-Methylpropyl)-8-[3-(trifluoromethyl)phenyl]-3H, 6H-1,4,5a,8a-tetraazaacenaphthylen-3-one], is a nootropic agent used to treat senility and is disclosed in co-pending, commonly-assigned Ser. No. 158,448, filed Feb. 22, 1988, which is incorporated by reference.

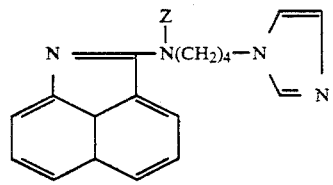
C

The compound C [N,[4-(1H-imidazol-1-yl)butyl]-benz[cd]indol-2-amine], is an antihypertensive agent and is disclosed in commonly-assigned U.S. Pat. No. 4,728,663, which is incorporated by reference.

Many members of the cephalosporin, penicillin and quinoline groups of antibiotics are amphoteric, having both amino and carboxylic acid functions and, in fact, are administered as their carboxylate salts. Aqueous solutions of these carboxylate salts are basic, but after injection they are brought to near-neutrality by the buffering action of body fluids, thus forming zwitterions which often have especially low solubilities. This situation is the reverse from, but similar to, that of the above salts of nitrogenous bases which have no carboxyl groups. In both situations, the drugs can precipitate near the injection site as they approach physiological pH near pH 7.4.

We have now discovered that, for parenteral use, drugs with basic primary or secondary nitrogen atoms (>NH) may be solubilized to remain in solution at physiological pH values near 7.4 by conversion to pro-drug forms which are salts of the corresponding phosphoramidic acid

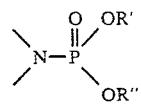

where R' and R" are the same or different and are hydrogen or a pharmaceutically acceptable cation. Examples of such cations are sodium, potassium and ammonium.

Drugs with basic primary or secondary nitrogen atoms which may be converted to pro-drugs in accordance with this invention include compounds with amine, amidine, guanidine, isourea, isothiourea and biguanide functions. These drug molecules may contain one or more of the above-mentioned basic functions or combinations thereof.

When a drug having one or more primary or secondary basic nitrogen atoms is phosphorylated, a pro-drug of the formula $B(Q)_n$ is obtained, wherein B is the residue formed by removal of a hydrogen atom from one or more nitrogen atoms of the above-mentioned basic functions, n is an integer representing the number of such nitrogen atoms in the compound, and each Q may be hydrogen or A wherein A is

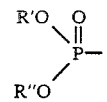

such that R' and R" may be the same or different and are R (where R is $C_1$-$C_6$ alkyl, aryl, aralkyl, heteroaryl, NC—$CH_2CH_2$—,

$Cl_3C$—$CH_2$— or $R_7OCH_2CH_2$, where $R_7$ is hydrogen or $C_1$-$C_6$ alkyl), hydrogen, or a pharmaceutically acceptable cation or R' and R" are linked to form a —$CH_2CH_2$— or

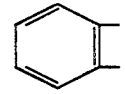

group, such that at least one Q is A. Therefore, when n is one, the pro-drug formed is A—B.

Except for the amines, each of the above-mentioned basic functions may be capable of a tautomeric shift during the phosphorylation reaction, such that the phosphoryl group may be linked to a nitrogen two atoms away from the nitrogen atom from which the hydrogen atom is removed.

After injection, such phosphoramidic acid salts reduce or totally avoid adverse local reactions near the site of injection, are well dispersed and diluted throughout the mammalian body and are then soon hydrolyzed to regenerate the active form (>NH) of the drug. Even with drugs which do not precipitate after injection, such pro-drugs can also avoid adverse reactions due to locally high drug concentrations in solution. In either case, use of the pro-drugs avoids both the use of long-line catheters to large central veins and administration of highly dilute solutions by slow intravenous drip over long time periods, procedures which involve hospitalization, discomfort, inconvenience, delay and expense. The by-product from pro-drug hydrolysis, a salt of phosphoric acid, is an innocuous normal bodily constituent.

It is probable that most of the hydrolysis of the phosphoramidic pro-drug of bis(2-imidazolin-2-ylhydrazone) of 9,10-anthracenedicarboxaldehyde ("bisantrene") is enzymatic and occurs in some bodily cellular compartments because hydrolysis was not observed or was very slow in water at pH 7.4, in whole blood or in blood plasma.

The relative stability of water solutions of phosphoramidic salts facilitates the manufacture and formulation of these pro-drugs. Because of the known susceptibility to hydrolysis of phosphoramidic acids under acidic conditions, such conditions are avoided or minimized in carrying out this invention.

Phosphoramidic acids can be stable for long periods when kept dry. They may be synthesized directly from the >NH— containing free base of the drug, using polyphosphoric acid or phosphorus oxychloride as phosphorylating agents, followed by selective hydrolysis of excess P—O—P or P—Cl moieties. However, it is generally more desirable to use a doubly blocked, monofunctional phosphorylating agent such as a phosphoric diester,

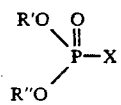

where X is an electronegative group such as halogen, —N₃, —CN,

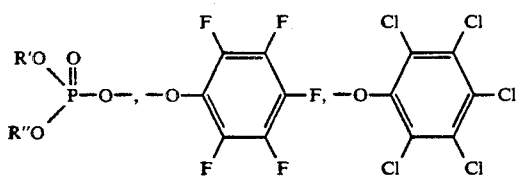

and the like, and R' and R" are the same or different and are C₁-C₆ alkyl, aryl, aralkyl, heteroaryl, NC—CH₂—CH₂—,

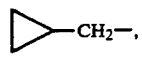

Cl₃C—CH₂— or R₇OCH₂CH₂—, where R₇ is hydrogen or C₁-C₆ alkyl, or R' and R" are linked to form a —CH₂—CH₂— or

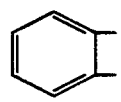

group.

The blocking R' and R" groups are chosen so as to be selectively removable under mild conditions in a subsequent step. In fact, the deblocking groups may be chosen so as to remove only one of the two blocking groups, when the blocking groups are different, thereby producing a phosporamidic monoester. Methods of synthesizing and deblocking phosphoric esters are described in L. A. Slotin, Synthesis, 737 (1977) and Y. Mizuno, The Organic Chemistry of Nucleic Acids, 161, Elsevier Publishers, New York (1986), which are hereby incorporated by reference.

The reaction sequence is thus:

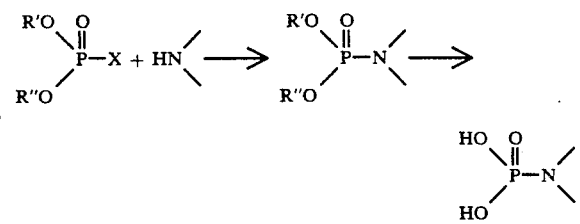

The initial step of phosphorylation of the drug is carried out in the presence of an aprotic organic solvent such as dimethylformamide, methylene chloride or the like. Some representative blocking groups and reagents to remove them are as follows:

| Blocking Group (R) | Deblocking Agent |
|---|---|
| NC—CH₂—CH₂— | Mild alkali |
| ▷—CH₂— | Hydrogen/noble metal catalyst |
| C₆H₅—CH₂— | Hydrogen/noble metal catalyst |
| C₆H₅— | CsF₂ or (C₂H₅)₄NF |
| Cl₃CH₂CH₂— | Zinc/aq. acetic acid |
| C₁-C₆ alkyl, | (CH₃)₃SiI, (CH₃)₃SiBr, |
| C₆H₅—CH₂— | or NaI/(CH₃)₃SiCl |
| (RO)₂ is —CH₂—CH₂— | Weak acid or (CH₃)₃N |
| (RO)₂ is ⌬ | Br₂ in H₂O |

In addition to the representative compounds just set forth, classes of blocking groups include aryl, aralkyl and heteroaryl, which may be deblocked in vivo by enzymatic degradation. This may occur even when chemical deblocking is not achieved. Triphenylphosphine may be used as a scavenger for halogen by-products formed during chemical deblocking with trimethylsilyl halides.

We have also found that diethyl chlorophosphate was an especially appropriate reagent for the diphosphorylation of bisantrene, thereby serving to facilitate its use as an antitumor agent, while minimizing phlebitis at the site of injection.

Even more preferred phosphorylating agents are the cyanophosphonates (X=CN). These compounds can provide excellent yields in a simple procedure without the need for a scavenger for acid by-product. A particularly preferred compound is diethyl cyanophosphonate.

The following drugs (Z=H, such that when one hydrogen is removed from one or more basic nitrogen atoms to form the pro-drug, the drug residue is B in the aforementioned formula B(Q)ₙ) are nitrogenous bases which are less than satisfactorily soluble for parenteral use (compounds A,B,C) and/or cause clinical phlebitis (compounds E,G,L,N,O,P below; see, e.g., Drugs of the Future, 13, 178, 192 (1988) as to compounds O and P), local irritation when dosed intravenously (compound Q below) and local necrosis (compound G below) after injection. These objectionable effects are reduced or eliminated by: (1) chemical conversion in accordance with this invention to phosphoramidic pro-drugs $$\left(Z = \overset{O}{\underset{OR''}{\overset{\|}{P}}}\overset{OR'}{\diagdown} \text{ or } \overset{O}{\underset{OH}{\overset{\|}{P}}}\overset{O^-}{\diagdown}\right)$$

by the procedures described above, wherein R' and R" may variously be hydrogen or R as defined above; and (2) in vivo hydrolysis of the P—N linkage of such phosphoramidic pro-drugs.

Additional examples of drugs that may be converted to the pro-drugs of this invention are as follows, with formulae set forth hereinafter:

Compound D—Cephalosporins ($R_8$=H, $$-\overset{O}{\underset{}{\overset{\|}{C}}}CH_3,$$

heterocyclic or -S-heterocyclic, $R_9$ is alkyl or alkylcarbonyl, $R_{10}$ is hydrogen, $C_1$-$C_6$ alkyl, phenoxy or substituted phenoxy)

Compound E—Ceftizoxime

Compound F—Tetracyclines ($R_{11}$=alkyl; $R_{12,R12a}$=H, $R_{12}$ is $CH_2$— and $R_{12a}$ is —OH, or there is a =$CH_2$ group in place of $R_{12}$ and $R_{12a}$)

Compound G—Doxorubicin ($R_{13}$=—OH) and related compounds ($R_{13}$=H or $$-\overset{O}{\underset{}{\overset{\|}{O}C}}Y,$$

where Y=$C_1$-$C_6$ alkyl)

Compound H—Gentamicin $C_1$($R_{14}$=$R_{15}$=$CH_3$), $C_2$ ($R_{14}$=$CH_3$, $R_{15}$=H), $C_{1a}$($R_{14}$=$R_{15}$=H)

Compound I—Amikacin

Compound J—Sisomycin

Compound K—Quinolones ($R_{16}$)50 H, halogen, $C_1$-$C_3$ alkyl; $R_{17}$=methyl, ethyl, cyclopropyl, substituted phenyl or —$NHCH_3$; $R_{18}$ is hydrogen, $C_1$-$C_6$ alkyl, —CH=CH—, phenyl, benzyl, $R_{19}$—O—$R_{20}$ (where $R_{19}$ is straight or branched chain $C_1$-$C_4$ alkyl and $R_{20}$ is hydrogen, straight or branched chain $C_1$-$C_4$ alkyl or aryl), $$R_{21}-\overset{O}{\underset{}{\overset{\|}{C}}}-O-\overset{R_{22}}{\underset{}{\overset{|}{C}H-}}$$

(where $R_{21}$ is hydrogen, straight or branched chain alkyl or aryl and $R_{22}$ is hydrogen or $C_1$-$C_4$ alkyl), $$\left\langle\underset{}{\overset{}{\bigcirc}}N-R_{23}-\right.$$

(where $R_{23}$ is $C_1$-$C_3$ alkylene), NC—$CH_2$—, $CH_3$—$SO_2$—$CH_2$—, $$CH_3-\overset{O}{\underset{}{\overset{\|}{C}}}-CH_2-, \quad -R_{24}-O\overset{O}{\underset{}{\overset{\|}{C}}}-\overset{R_{25}}{\underset{}{\overset{|}{C}H-}}$$

(where $R_{24}$ and $R_{25}$ are straight or branched chain $C_1$-$C_4$ alkyl)

[ring structures shown]

$m$=0-2 and $p$=1 or 2, such that when $m$=0, $p$=2.

Compound L—Ciprofloxacin (where in Compound K, $R_{16}$=H, $R_{17}$=cyclopropyl, $R_{18}$=H and $m$=0)

Compound M—Quinolones ($R_{16}$=H, F; $R_{17}$=methyl, ethyl, cyclopropyl, substituted phenyl or —$NHCH_3$)

Compound N—Amsacrine

Compound O—Piritrexin

Compound P—3-Deazaguanine

Compound Q—Emetine

Compound R—Stilbenediamidines ($R_{26}$ and $R_{27}$ are H, OH or halogen); Hydroxystilbamidine (where $R_{26}$ is 2-hydroxy in the ring and $R_{27}$ is H)

Compound S—Alkylenedioxybisbenzamidines ($q$=1-7); Pentamidine (where $q$=5)

Compound T—Bisantrene

Compound U—Diminazene

Compound V—Imidocarb

Compound W—Nafamstat

Compound X—Mitoguazone

Compound Y—Tacrine

D

[structure of cephalosporin D]

E

[structure of ceftizoxime E]

-continued
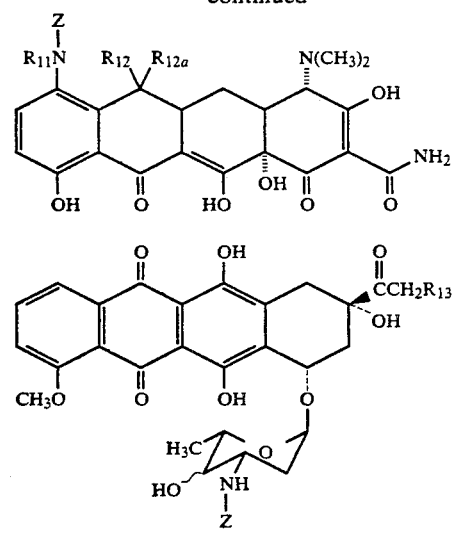
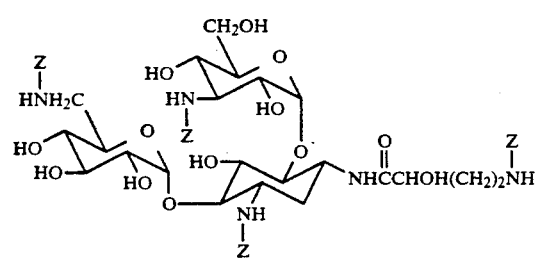
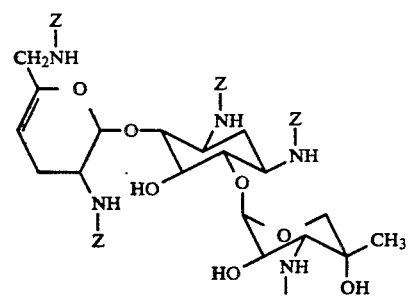
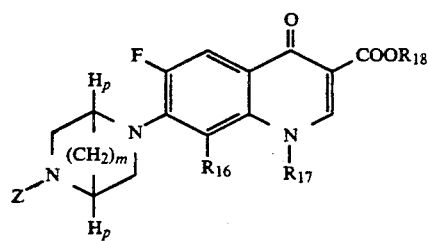
-continued
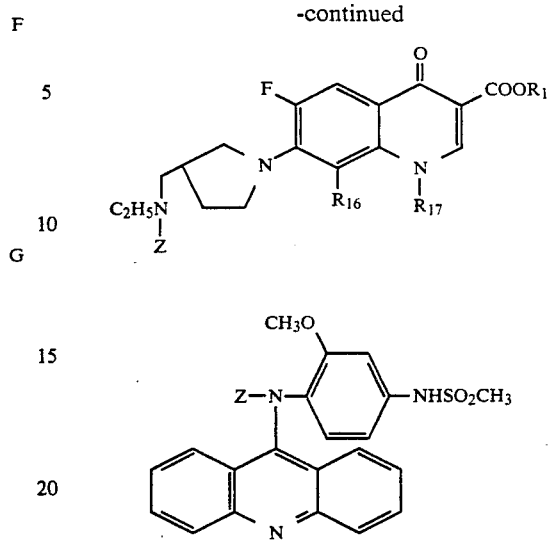
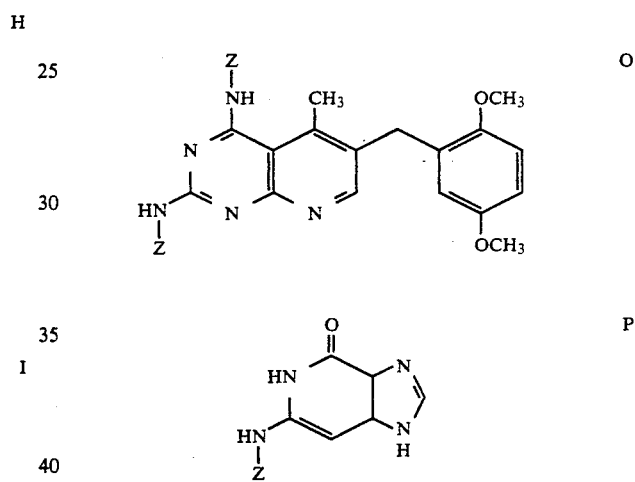
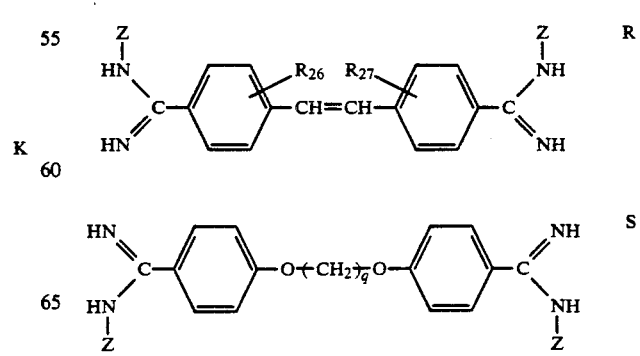

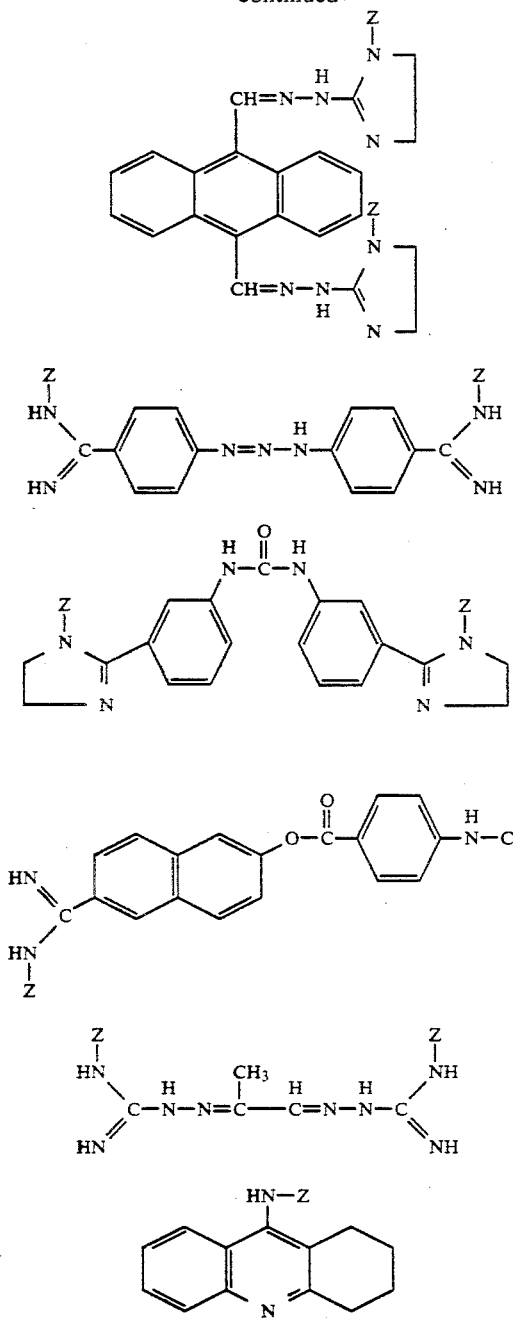

Before phosphorylation, the carboxylic acid and hydroxyl functions are protected by conversion to trimethylsilyl esters and ethers, using N,O-bis(trimethylsilyl)acetamide or N,O-bis(trimethylsilyl)trifluoroacetamide. The silyl groups are then removed by reaction with traces of water during isolation of the phosphorylated intermediates.

In general, when X is halogen in the phosphorylating agent, a tertiary amine or a silyl-containing compound such as a N,O-bis(trimethylsilyl)acetamide or N,O-bis(trimethylsilyl)trifluoroacetamide is used to scavenge the hydrogen halide released during the reaction with the drug.

In yet another aspect of this invention, the blocked, phosphorylated presursors (Z= of the water-solubilized pro-drugs described previously are contemplated to have pro-drug efficacy of a different type, since, for example, the blocked bisantrene derivatives also have antitumor activity.

Instead of being polar compounds soluble in water at pH 7.4, these precursors have enhanced lipid solubility, enabling enhanced absorption after oral dosage. They may also be injected intravenously, subcutaneously or intramuscularly as lipid emulsions. Depending on the drug selected, the body organ involved and the blocking groups, subsequent gradual bioconversions regenerate the parent drug at various rates, either directly via initial hydrolysis of the P—N bond, or in a step-wise manner via initial hydrolysis of P—O bonds. By appropriate choice of blocking groups, it is contemplated that beneficial selectivities will be achieved in pharmacokinetics and pharmacodynamics (organ targeting) via such lipid-solubilized pro-drugs. It is also believed that such pro-drugs will also increase the passage through the blood-brain barrier.

Both the water-solubilizing and lipid solubilizing pro-drugs of this invention may be administered in association with conventional pharmaceutically acceptable carriers.

This invention will be described in greater detail in conjunction with the following specific examples.

EXAMPLE 1

Bis(2-imidazolin-2-ylhydrazone) of 9,10-anthracenedicarboxaldehyde

To a solution of 60.0 g of bis(2-imidazolin-2-hlhydrazone) of 9,10-anthracenedicarboxaldehyde dihydrochloride (prepared as described in U.S. Pat. No. 4,258,181) in 1400 ml of water was added a solution of 27.0 g of sodium carbonate in 400 ml of water, with vigorous swirling. The resulting suspension was allowed to stand 5 hours, then the solid was collected in a three-liter, coarse porosity sintered glass funnel and washed with three 1.2 liter portions of very dilute aqueous ammonia, at a concentration of 2.0 ml of concentrated ammonia per liter. The ammonia solution enabled satisfactorily rapid filtration by lowering surface tension and preventing peptiation of the solid. The last wash was chloride-free and gave 47.2 g of the desired product as a light orange solid, mp 307°–308° C.

EXAMPLE 2

2,2'-(9,10-Anthracenediylbis(methylidyne-1-hydrazinyl-2-ylidene)]bis4,5-dihydro-1-(1-oxobutyl)-1H-imidazole]

To a stirred suspension of 3.19 g of bis(2-imidazolin-2-ylhydrazone) of 9,10-anthracenedicarboxaldehyde dried in vacuo at about 110° C. for about 15 hours) in 100 ml of N,N-dimethylformamide (dried over 4A molecular sieves), was added 12.66 g of butyric anhydride. All of the solid was dissolved after stirring for 20 minutes. The solution was filtered through a sintered glass funnel. The filtrate was allowed to stand 26 hours at about 23° C. as a crystalline solid separated. The solid was collected by filtration, washed with N,N-dimethyl-

EXAMPLE 3

2,2'[9,10-Anthracenediylbis(methylidene-1-hydrazinyl-2-ylidene)]bis[4,5-dihydro-gamma-oxo-1H-imidazole-1-butanoic Acid]

A suspension of 3.19 g of bis(2-imidazolin-2-yl-ydrazone) of 9,10-anthracenedicarboxaldehyde (dried in vacuo at 111° C. for 15 hours) and 4.80 g of succinic anhydride in 100 ml of dried N,N-dimethylformamide was stirred for 40 minutes, when the solid had dissolved. the hazy solution was filtered and the filtrate allowed to stand at 23° C. for 24 hours. The filtrate was diluted with 500 ml of water and the resulting slightly warm solution was immediately chilled in an ice bath, producing small granular orange crystals and a finely divided yellow colloid. The colloid was decanted and the granular crystals were washed four times by decantation with cold water, then collected by filtration to give 2.84 g of the desired product as an orange solid, mp 129°–133° C.

EXAMPLE 4

[9,10-Anthracenediylbis[methylidyne-1-hydrazinyl-2-ylidene (4,5-dihydro-1H-imidazole-2,1-diyl)]]bisphosphonic Acid, Tetraethyl Ester To a stirred suspension of 7.969 g of dried bis-(2-imidazolin-2-ylhydrazone) of 9,10-anthracenedicarboxaldehyde in 400 ml of dried dichloromethane under argon was added with stirring via hypodermic syringes and a rubber septum, first 8.137 g of N,O-bis(trimethylsilyl)acetamide, then 6.902 g of diethyl chlorophosphate. The solid all dissolved after stirring for about 3 hours. The solution was filtered through 200 g of dry-packed, air-equilibrated neutral alumina, (ICN, "for dry-column chromatography") in a 3.8 cm×18 cm column. The colored part of the eluate was collected (cut 1) and the column was eluted with an additional 5×200 ml of dichloromethane to obtain cuts 2–6. Cuts 1–4 were combined and concentrated to 40 ml, then 100 ml of toluene was gradually added to the boiling mixture, with swirling, as a crystalline solid separated and the volume boiled down to 100 ml with bp 100° C. The solid which crystallized was washed with toluene, then with methanol to give 4.36 g of the desired product as orange needles, mp 217° C.

EXAMPLE 5

[8,10-Anthracenediylbis[methylidyne-1-hydrazinyl-2-ylidene (4,5-dihydro-1H-imidazole-2,1-diyl)]]bisphosphonic Acid, Tetraphenyl Ester To a stirred suspension of 1.99 g of dried bis-(2-imidazolin-2-ylhydrazone) of 9,10-anthracenedicarboxaldehyde in 100 ml of dried dichloromethane were added, under argon as described in Example 4, 2.03 g of N,O-bis(trimethylsilyl)acetamide "BSA" and 2.68 g of diphenyl phosphorochloridate. After one hour of stirring all of the solid had dissolved. Stirring was continued for 2 hours longer. The reaction solution was poured into a 3.8 cm×18 cm dry column of 200 g of air-equilibrated alumina. The column was developed with dichloromethane and the first 100 ml of colorless eluate was discarded, then as the first yellow band neared the bottom, elution cuts of 100 ml each were collected and evaporated. The residue from the first cut, 1.74 g, was dissolved in about 13 ml of dichloromethane, then 40 ml of toluene was added and the solution was heated to boil off the dichloromethane, reduce the volume to about 25ml and crystallize a solid. The solid was collected by filtration and washed with toluene, then with ether to give 1.65 g of the desired product as an orange solid, mp 214°–215° C.

EXAMPLE 6

[9,10-Anthracenediylbis[methylidyne-1-hydrazinyl-2-ylidene (4,5-dihydro-1H-imidazole-2,1-diyl)]]bisphosphonic Acid To a stirred orange solution of 8.74 g of the tetraethyl ester of [9,10-anthracenediylbis[methylidyne-1-hydrazinyl-2-ylidene(4,5-dihydro-1H-imidazole-2,1-diyl)]]-bis phosphonic acid in 150 ml of dried dichloromethane under argon was added 13.0 g of iodotrimethylsilane via a glass hypodermic syringe and rubber septum. There was a slight exothermic reaction to about 40° C. and the solution became yellow. Within 5 minutes it was orange again. After 30 minutes the solution was evaporated to dryness in vacuo. The glassy residue solidified when suspended in 150 ml of acetone containing 5.2 ml of water to hydrolyze the intermediate silyl ester. The suspension was stirred for 16 hours. The solid was collected and washed with acetone to give 8.17 g of yellow solid. This solid was recrystallized by dissolving it in 200 ml of triethylamine, thus forming a soluble phosphoramidic acid salt. The free phosphoramidic acid was precipitated by adding 1.82 ml of 97% formic acid. The solid was collected by filtration and washed with ethanol to give 6.04 g of yellow solid which turned orange when dried, mp 235°–238° C.

EXAMPLE 7

2,2'-(9,10-Anthracenediyldimethylidyne)bis[1-(1-benzoyl-4,5-dihydro-1H-imidazol-2-yl) hydrazide] of Benzoic Acid The procedure of Example 4 was followed while reacting 1.99 g of dried bis(2-imidazolin-2-ylhydrazone) of 9,10-anthracenedicarboxaldehyde, 2.034 g of N,O-bis(trimethylsilyl)acetamide and 1.406 g of benzoyl chloride in 100 ml of dried dichloromethane. The suspension was stirred for 2 days at 24° C. and then was filtered to remove some insoluble orange solid which was washed with dichloromethane. The filtrate and washes were passed through 50 g of air-equilibrated alumina in a 2.3 cm×13.0 cm column. The initial colorless eluate was collected as cut 1. Further elution with dichloromethane gave 50 ml each of cuts 2–5. The eluates were evaporated and the residues from cuts 1 and 2 were washed with ether and combined to give 1.205 g of the desired product as an orange solid, mp 111°–114° C.

EXAMPLE 8

2,2'-[9,10-Anthracenediylbis(methylidyne-1-hydrazinyl-2-ylidene)]bis[4,5-dihydro-delta-oxo-1H-imidazole-1-pentanoic Acid]

A mixture of 3.19 g of bis(2-imidazolin-2-ylhydrazone) of 9,10-anthracenedicarboxaldehyde and 5.48 g of glutaric anhydride in 100 ml of dried N,N-dimethylformamide was stirred at 24° C. for 23 hours. The solution was evaporated in vacuo at 35° C. The residue was diluted with 20 ml of dry N,N-dimethyl formamide and swirled to dissolve the residue, then 100 ml of dry ether was added and the mixture was swirled and allowed to stand for several hours. The precipitate which formed was collected and washed with ether to give 4.81 g of the desired product as an orange solid, mp 218°–221° C.

EXAMPLE 9

2,2'-9,10-Anthracenediylbis(methylidyne-1-hydrazinyl-2-ylidene)]bis[4,5-dihydro]-1H-imidazole-1-carboxaldehyde To a stirred suspension of 3.98 g of dried bis-(2-imidazolin-2-ylhydrazone) of 9,10-anthracenedicarboxaldehyde in 50 ml of dried N,N-dimethylformamide was added 10.0 ml of phenyl formate. Stirring was continued for 37 hours at 21° C.; the red-orange suspension had gradually changed to yellow in the first hour. Filtration and washing with acetone gave 4.61 g of the desired product as a yellow solid, mp 280°–281° C.

EXAMPLE 10

2,2'-[9,10-Anthracenediylbis(methylidyne-1-hydrazinyl-2-ylidene)]bis[4,5-dihydro]-1H-imidazole-1-carboxylic Acid], Bis(1,1-dimethylethyl) Ester To a solution of 6.55 g of di-tert-butyl dicarbonate in 100 ml of dry N,N-dimethylformamide was added 3.98 g of dried bis(2-imidazolin-2-ylhydrazone) of 9,10-anthracenedicarboxaldehyde. The suspension was protected with a drierite tube (to allow by-product carbon dioxide to escape) and was stirred at 22° C. for 15 hours to give a yellow solution. A 60 ml portion of water was added to the solution until the first sign of turbidity. A clear gum (A) gradually separated. After standing for 2 hours the supernatant was decanted from the gum and filtered through a filter paper cone over about 16 hours. The filtrate gradually deposited orange crystals. After 24 hours the crystals were collected and washed twice with N,N-dimethylformamide/water, 25/10, then twice with water to give 1.29 g of yellow solid (B). The gum (A) crystallized on standing and this material was washed as for (B) above to give 0.59 g of yellow solid (C). The combined clear filtrate and the N,N-dimethylformamide/water wash from (B) above was diluted to 300 ml with water. The resulting emulsion was allowed to stand for 15 hours, then the agglomerated material was collected by filtration and washed with water to give 3.06 g of a yellow solid (D). A solution of combined yellow solids (B) and (C) 1.68 g in 10 ml of dichloromethane was chromatographed on 8.40 g of neutral alumina (ICN, "for dry-column chromatography") in a 1.0 cm×8.0 cm column, eluting with dicloromethane until the yellow band eluted. Evaporation of the eluate gave 1.81 g of a yellow glass. The glass was covered with 30 ml of petroleum ether and mixed, then was allowed to stand for 16 hours. The material recrystallized and was collected by filtration, and washed with ether to give 1.37 g of bis-(1,1-dimethylethyl)2,2'-[9,10-anthracenediylbis [methylidyne[1-[(1,1-dimethylethoxy)carbonyl-1-hydrazinyl-2-ylidene]]bis[4,5-dihydro-1H-imidazole-1-carboxylate] as a yellow solid, mp 190°–191° C.

A 2.94 g amount of the yellow solid (D) was washed three times with ether leaving 1.84 g of an orange solid. The orange solid (1.84 g) was pulverized and triturated with 50 ml of dichloromethane, the filtered. The orange solid on the filter was washed with dichloromethane. The filtrate and washes were combined and repeatedly refiltered through a pad of diatomaceous earth, then the filtrate was subjected to dry column chromatography on 200 g of air equilibrated silica gel (ICN Co., "for dry-column chromatography") in a 3.4×50.0 cm nylon column, developing the column with 200 ml of chloroform/methanol, 19/1. The fastest yellow band moved only to Rf 0.35 as solvent reached the bottom. The following bands were cut out and extracted on small fritted-glass funnels with chloroform/methanol, 3/1, and the extracts were evaporated to obtain the residues.

| Extract No. | RF of Band on Column (Color) | Residue Wt. | and Color |
|---|---|---|---|
| 1 | 0.0–0.05 (tan) | 0.02 g | Yellow Solid |
| 2 | 0.06–0.15 (light orange) | 0.03 g | Pale orange solid |
| 3 | 0.16–0.25 (light yellow) | 0.44 g | Orange solid |
| 4 | 0.26–0.35 (orange tan) | 0.81 g | Orange solid |

The residue of extract 4, 0.81 g was dissolved in 5.0 ml of dichloromethane, then was filtered and the filtrate evaporated to give a glassy residue. The residue was swirled with about 20 ml of ether and allowed to stand. Then the solid was collected and washed with ether to give 0.50 g of the desired product as a yellow orange solid, mp 148°–151° C.

EXAMPLE 11

2,2'-[9,10-Anthracenediylbis(methylidyne-1-hydrazinyl-2-ylidene)]bis[4,5-dihydro-1-[(4-methylphenyl)sulfonyl]-1H-imidazole]

The procedure of Example 4 was followed while reacting 1.99 g of dried bis(2-imidazolin-2-ylhydrazone) of 9,10-anthracenedicarboxaldehyde, 2.034 g of N,O-bis(trimethylsilyl)acetamide and 1.91 g of p-toluenesulfonyl chloride in 100 ml of dried dichloromethane. The suspension was stirred at 24° C. for 44 hours, then was filtered to remove some insoluble orange solid, and washed with dichloromethane. The filtrate and washes were passed through 50.0 g of air-equilibrated alumina. The initial colorless eluate was discarded and additional dichloromethane was added as seven 50 ml cuts were collected. The first two cuts were evaporated and the residue washed sparingly with chloroform to give 1.10 g of the product of the example, mp 255°–258° C.

EXAMPLE 12

2,2'-[9,10-Anthracenediylbis[methylidyne-1-hydrazinyl-2-ylidene (4,5-dihydro-1H-imidazole-2,1-diyl)carbonyl]]biscyclohexanecarboxylic Acid A suspension of 3.19 g of bis(2-imidazolin-2-ylhydrazone) of 9,10-anthracenedicarboxaldehyde and 5.4 g of trans-1,2-cyclohexanedicarboxylic anhydride in 100 ml of dried N,N-dimethylformamide was stirred at 24° C. for 3 hours. The clear solution was concentrated in vacuo to near dryness then was slurried with 100 ml of ether. The solid that formed was collected by filtration, washed with ether and dried in vacuo to give 6.7 g of the desired product.

EXAMPLE 13

2,2'-(9,10-Anthracenediyldimethylidyne)bis[1-[4,5-dihydro-1-(methoxyacetyl)-1H-imidazol-2-yl]hydrazide of Methoxyacetic Acid thylformamide with stirring for 12-74 hours, then employing column chromatography on alumina (neutral), Bio Sil A or silica gel and elution with a solvent such as dichloromethane, dichloromethane/methanol, acetone and the like to separate the desired product.

TABLE IV

| Ex. | Acid chloride | Product Name | Yield (g) | MP° C. |
|---|---|---|---|---|
| 14 | 4-hexylbenzoyl chloride | 2,2'-(9,10-Anthracenediyldimethylidyne)bis[1-[1-(4-hexylbenzoyl)-4,5-dihydro-1H-imidazol-2-yl]hydrazide] of 4-hexylbenzoic acid | 4.347 | 83-98 |
| 15 | 3-nitrobenzoyl chloride | 2,2'(9,10-Anthracenediyldimethylidyne)bis[1-[4,5-dihydro-1-(3-nitrobenzoyl)-1H-imidazol-2-yl]hydrazide] of 3-nitrobenzoic acid | 1.913 | 162-175 |
| 16 | 2-furoyl chloride | 2,2'-(9,10-Anthracenediyldimethylidyne)bis[1-[1-(2-furanylcarbonyl)-4,5-dihydro-1H-imidazol-2-yl]hydrazide] of 2-furancarboxylic acid | 2.310 | 210-213 |
| 17 | 4-methoxybenzoyl chloride | 2,2'-(9,10-Anthracenediyldimethylidyne)bis[1-[4,5-dihydro-1-(4-methoxybenzoyl)-1H-imidazol-2-yl] hydrazide] of 4-methoxybenzoic acid | 1.332 | 209-211 |
| 18 | 4-cyanobenzoyl chloride | 2,2'-(9,10-Anthracenediyldimethylidyne)bis[1-[1-(4-cyanobenzoyl)-4,5-dihydro-1H-imidazol-2-yl] hydrazide] of 4-cyanobenzoic acid | 0.510 | 178-185 |
| 19 | pentafluorobenzoyl chloride | 2,2'-(9,10-Anthracenediyldimethylidyne)bis[1-[4,5-dihydro-1-(pentafluoro-1H-imidazol-2-yl)hydrazide] of pentafluorobenzoic acid | 1.190 | 145-150 |
| 20 | tert.-butylacetyl chloride | 2,2'-(9,10-Anthracenediyldimethylidyne)bis[1-[1-(3,3-dimethyl-1-oxobutyl)-4,5-dihydro-1H-imidazol-2-yl]-hydrazide] of 3,3-dimethylbutanoic acid | 1.682 | 90-99 |
| 21 | 2-fluorobenzoyl chloride | 2,2'-(9,10-Anthracenediyldimethylidyne)bis[1-[1-(2-fluorobenzoyl)-4,5-dihydro-1H-imidazol-2-yl] hydrazide] of 2-fluorobenzoic acid | 3.383 | 167-175 |
| 22 | 2-naphthyl chloride | 2,2'-(9,10-Anthracenediyldimethylidyne)bis[1-[4,5-dihydro-1-(2-naphthalenylcarbonyl)-1H-imidazol-2-yl]-hydrazide] of 2-naphthoic acid | 2.147 | 175-182 |
| 23 | acetyl chloride | 2,2'-(9,10-Anthracenediyldimethylidyne)bis[1-(1-acetyl-4,5-dihydro-1H-imidazol-2-yl)hydrazide] of acetic acid | 1.184 | 233-235 |
| 24 | butyryl chloride | 2,2'-(9,10-Anthracenediyldimethylidyne)bis[1-[4,5-dihydro-1-(1-oxobutyl)-1H-imidazol-2-yl]hydrazide] of butanoic acid | 2.220 | 190-193 |

The procedure of Example 4 was followed while reacting 1.99 g of dried bis(2-imidazolin-2-ylhydrazone) of 9,10-anthracenedicarboxaldehyde, 4.069 g of N,O-bis(trimethylsilyl)acetamide and 2.17 g of methoxyacetyl chloride in 100 ml of dried dichloromethane. The reaction mixture was allowed to stir at room temperature for 64 hours, then was filtered to remove some unreacted material and washed with dichloromethane. The filtrate and washes were chromatographed through 50 g of Bio Sil A (Bio-Rad Laboratories). The column was eluted first with 150 ml of dicloromethane for cuts 1 and 2, 250 ml of dichloromethane with 2% methanol for cuts 3 and 4, 100 ml of dichloromethane with 3% methanol for cuts 5 and 6, 100 ml of dichloromethane with 4% methanol for cut 7 and 100 ml of dichloromethane with 5% methanol for cut 8. The cuts were made by using visual observation to separate the three bands on the column. The cuts were evaporated in vacuo. The residue from cut 5 (1.635 g), derived from the largest (middle) band, was recrystallized from dichloromethane/tert-butyl methyl ether to give the desired product as a fine yellow powder, mp 225°-229° C.

EXAMPLES 14-24

Additional acid chloride acylation products of bis(2-imidazolin-2-ylhydrazone) of 9,10-anthracenedicarboxaldehyde listed in Table IV were prepared in the manner described by the procedures of Examples 4, 5 and 13, reacting the given acid chloride with 5 mmol of the above base compound in the presence of an acid binding agent such as N,O-bis(trimethylsilyl)acetamide in a dried solvent such as dichloromethane or N,N-dime-

EXAMPLE 25

2,2'-[9,10-Anthracenediylbis(methylidyne-1-hydrazinyl-2-ylidene)]bis[4,5-dihydro-1H-imidazole-1-sulfonic Acid], compound with N,N-diethylethanamine (1:2)

To a mixture of 1.99 g of dried bis(2-imidazolin-2-ylhydrazone) of 9,10-anthracenedicarboxaldehyde and 5.44 g of sulfur trioxide triethylamine complex was added 50 ml of dried N,N-dimethylformamide. The orange suspension was stirred at about 21° C. for 25 hours. The solid was collected by filtration, washed with N,N-dimethylformamide, then ether to give 2.42 g of the desired product as a light orange solid, mp 285°-290° C.

EXAMPLE 26

2,2'-[9,10-Anthracenediylbis(methylidyne-1-hydrazinyl-2-ylidene)]bis[4,5-dihydro-alpha-oxo-1H-imidazole]propanesulfonic Acid]

When a suspension of dried bis(2-imidazolin-2-ylhydrazone) of 9,10-anthracenedicarboxaldehyde and two equivalents of 3-sulfopropionic anhydride [M. S. Kharasch and H. C. Brown, J. Amer. Chem. Soc., 62, 925 (1940)] in 100 ml of dried N,N-dimethylformamide is reacted by the procedure of Example 3 the product of the example is obtained.

EXAMPLE 27

2,2'-[9,10-Anthracenediylbis(methylidyne-1-hydrazinyl-2-ylidene)]bis[4,5-dihydro-N,N,N-trimethyl-3-oxo-1H-imidazole-1-ethanaminium]dichloride To 3.98 g of dried bis(2-imidazolin-2-ylhydrazone) of 9,10-anthracenedicarboxaldehyde and 5.13 g of chloroacetic anhydride Was added 100 ml of dried N,N-dimethylformamide. The mixture was swirled for one minute, when all solids had dissolved. After 10 minutes, 45 ml of a solution of 5.0 g of trimethylamine in 100 ml of acetonitrile was added with stirring, causing a slight rise in temperature. After 10 minutes a gummy solid began to separate. After standing for 17 hours the supernatant liquid was decanted and the residual solid was washed by decantation with two 5 ml portions of N,N-dimethylformamide, then was dried in vacuo to give the desired product as an orange solid.

EXAMPLE 28

2,2'-[9,10-Anthracenediylbis(methylidyne-1-hydrazinyl-2-ylidene)]bis[1-acetyl-4,5-dihydro-1H-imidazole To a suspension of 1.992 g of dried bis(2-imidazolin-2-ylhydrazone) of 9,10-anthracenedicarboxaldehyde in 100 ml of dried dichloromethane was gradually added 8.0 ml of acetic anhydride. The solid all rapidly dissolved and then a yellow solid immediately began to separate. After five hours the solid was collected and washed with dichloromethane to give 1.98 g of the desired product as a yellow solid, mp 296°–299° C.

EXAMPLE 29

2-[[10-[[Acetyl(1-acetyl-4,5-dihydro-1H-imidazol-2-yl)hydrazono]methyl]-9-anthracenyl]methylene]-1-(4,5-dihydro-1H-imidazol-2-yl) hydrazide of Acetic Acid To a suspension of 1.992 g of dried bis-(2-imidazolin-2-ylhydrazone) of 9,10-anthracenedicarboxaldehyde in 100 ml of dried N,N-dimethylformamide was added 5.0 ml of acetic anhydride. In 15 minutes all of the solid had dissolved and yellow crystals began to separate. After 4 hours the solid was collected and washed three times with dry N,N-dimethylformamide. The filtrate and washes were combined and evaporated in vacuo. The residue was re-evaporated three times with 10 ml portions of dry N,N-dimethylformamide, then dried finally at 60° C. in vacuo to remove a trace odor of acetic anhydride. The residue was agitated with 25 ml of dichloromethane and the undissolved solids were removed by filtration. The filtrate was evaporated to give a slightly tacky, glassy residue that hardened while standing under 25 ml of dry ether for 16 hours. The solid was collected and washed with ether to give 0.97 g of the desired product as a yellow solid, melting at 283° C.

EXAMPLE 30

2,2'-[9,10-Anthracenediylbis[methylidyne(1-formyl-1-hydrazinyl-2-ylidene)]]bis4,5-dihydro-1H-imidazole-1-carboxaldehyde]

A magnetically stirred suspension of 3.98 g of dried bis(2-imidazolin-2-ylhydrazone) of 9,10-anthracenedicarboxaldehyde in 100 ml of dried N,N-dimethylformamide was maintained at 3°–5° C. with an ice bath during the portionwise addition, over a 5 minute period, of 8.29 g of freshly prepared trimethylacetic formic anhydride 15 [E. J. Vlietstra, et al., Res. Trav. Chim., 101, 460 (1982), kept at −80° C. as a solid, then thawed just before use]. Within another 5 minutes all of the solid had dissolved to give a hazy solution. The solution was filtered and the filtrate was allowed to stand at 23° C. for 64 hours. The crystals which had separated were collected and washed with acetone to give 5.11 g of the desired product as yellow-orange crystals, mp 296°–301° C. (dec.).

EXAMPLE 31

[S-(R*,R*)][9,10-Anthracenediylbis[methylidyne-1-hydrazinyl-2-ylidene
(4,5-dihydro-1H-imidazole-2,1-diyl)
(1-methyl-2-oxo-2,1-ethanediyl)]]bis carbamic Acid,
Bis(1,1-dimethylethyl) Ester A suspension of 3.985 g of dried bis(2-imidazolin-2-ylhydrazone) of 9,10-anthracenedicarboxaldehyde in 200 ml of dried dichloromethane containing 12.068 g of tert-butyl-oxycarbonyl-L-alanine-O-succinimide was sonicated at 18°–23° C. for 3 hours and then filtered, washing with dichloromethane. The filtrate was chromatographed on 100 g of aluminum oxide, eluting with dichloromethane. After the eluate became yellow, the next 225 ml was evaporated. The residue was dissolved in 200 ml of dimethylformamide at 13° C. To this was added 5.48 ml of N-methylmorpholine and then a solution of 2.25 g of glycine in 20 ml of water to destroy excess acylating agent. The resulting solution was stirred at 23° C. for 40 minutes, then chilled in an ice bath and diluted with 600 ml of ice cold water. The solid was collected and washed with water, giving 4.69 g of the desired product, mp 148°–155° C.

EXAMPLE 32

[S-(R*,R*)][9,10-Anthracenediylbis(methylidyne-1-hydrazinyl-2-ylidene)]bis[1-(2-amino-1-oxopropyl)-4,5-dihydro-1H-imidazole]tetrahydrochloride A solution of 4.13 g of [S-(R*,R*)[9,10-anthracenediylbis [methylidyne-1-hydrazinyl-2-ylidene-(45-dihydro-1H-imidazole-2,1-diyl) (1-methyl-2-oxo-2,1-ethanediyl)]]bis carbamic acid, bis(1,1-dimethylethyl) ester in 40 ml of glacial acetic acid and 20 ml of anisole was cooled in a water bath at 16° C. as hydrogen chloride was bubbled in for 3 minutes. After standing for 30 minutes the solid was collected, washed with two 35 ml portions of glacial acetic acid and four times with acetone, giving 3.61 g of the desired product, mp 205°–208° C.

EXAMPLE 33

2,2'[9,10-Anthracenediylbis(methylidene-1-methyl-1-hydrazinyl-2-ylidene)]bis[4,5-dihydro-gamma-oxo-1H-imidazole]-1-butanoic Acid A suspension of 16.2 g of bis(2-imidazolin-2-ylmethylhydrazone) of 9,10-anthracenedicarboxaldehyde dihydroiodide in water was stirred with 12.0 g of sodium carbonate at 50°–70° C. for one hour, then cooled. The solid was washed with water and dried to give 9.8 g of the free base. Subsequent acylation with succinic anhydride by the procedure of Example 3 gives the title compound as an orange solid.

EXAMPLE 34

[9,10-Anthracenediylbis[methylidyne-1-hydrazinyl 2-ylidene (4,5-dihydro-1H-imidazol-2,1-diyl)]]phosphonic Acid, Diethyl Ester To a 3 liter round bottom flask equipped with a stirring bar was added, under argon, 41.456 g of the bis(2-imidazolin-2-ylhydrazone) of 9,10-anthracenedicarboxaldehyde, (not specially dried and therefore hydrated), 2 liters of dichloromethane, 42.33 g (51.43 ml of N,O-bis(trimethylsilyl) acetamide via a syringe and 35.90 g (30.07 ml) of diethyl chlorophosphate also via a syringe. After stirring overnight, the cloudy orange mixture was filtered. The filtrate was chromatographed on 1 kg of partially deactivated (air equilibrated) alumina and developed with dichloromethane. Nine 1 liter fractions were taken and partially concentrated. Fractions 1-3 gave the product of Example 4. Fractions 4-7 were combined and further concentrated, giving 13.31 g of solid.

A 13.01 g portion of the above solid in a fritted funnel was washed sparingly with 30, 20 and 10 ml of dichloromethane and then with water, giving 6.50 g of orange solid. This solid was mixed with 200 ml of hot dichloromethane and filtered through 3 g of silica gel, washing with 40 ml of dichloromethane. The filtrate was concentrated to about 30 ml. The resulting solid was collected and washed with a minimum of cold dichloromethane and then with carbon tetrachloride, giving 4.50 g of the desired product as yellow leaflets, mp 195°-202° C. Thin layer chromatography on silica gel vs. chloroform/methanol (9/1), gave a spot with Rf 0.3 as compared with Rf 0.6 for the product of Example 4.

EXAMPLE 35

[9,10-Anthracenediylbis[methylidyne-1-hydrazinyl-2-ylidene (4,5-dihydro-1H-imidazol-2,1-diyl)]]phosphonic Acid Hydroiodide To a solution of 1.07 g of dried [9,10-anthracenediylbis [methylidyne-1-hydrazinyl-2-ylidene (4,5-dihydro-1H-imidazole-2,1-diyl)]]phosphonic acid, diethyl ester and 5.25 g of triphenylphosphine in 90 ml of dried dichloromethane, under argon, was added, via a syringe, 1.0 g (0.71 ml) of iodotrimethylsilane. After 30 minutes, the clear orange solution was evaporated to dryness and then re-evaporated twice from 50 ml portions of dry dichloromethane. The residue was suspended in 50 ml of acetone and 1 ml of water was added, precipitating an orange gum. The gum was pressed thin and allowed to stand overnight in the moist acetone under argon. The gum solidified. It was then pulverized, collected and washed with acetone, giving 1.21 g of the desired product as an orange solid; MS ((+)FAB) 507(M+H); NMR (300 MHz, Me$_2$SO-d$_6$:) δ 1.23 (t, 3, C—CH$_3$), 3.77 (s, NCH$_2$CH$_2$N), 3.85 (m, CH$_2$ of Et), 7.70 (h, 4, arom.), 8.44 and 8.49 (m, 4, arom.), 8.78 (s, 1, NH), 9.04 (s, 1, NH), 9.34 (s, 1, CH=N), 9.43 (s, 1, CH=N), 12.54 (s, 1, C=N'H+).

EXAMPLE 36

[2-[[[10-[[(4,5-Dihydro-1H-imidazol-2-yl) ethylhydrazono]methyl]-9-anthracenyl]methylene]hydrazino]-4,5-dihydro-1H-imidazol-1-yl]phosphonic Acid Hydroiodide The procedure of Example B was followed except that no triphenylphosphine was used to remove by-product ethyl iodide. A solution of the crude, solidified reaction product in 10 ml of methanol was filtered through 1 g of alumina in a 0.6 cm column, washing with 5 ml of methanol. The filtrate was evaporated almost to dryness when the residual syrup began to crystallize. A 20 ml portion of acetone was added, the solid was macerated and then allowed to stand overnight. The solid was collected and washed with acetone, giving 1.057 g of the desired product; MS ((+)FAB), 479(M+H); NMR (300 MHz, Me$_2$SO-d$_6$) δ 3.77 (s, 8, NCH$_2$CH$_2$N), 7.66 (m, 4, arom.), 8.49 (h, 4, arom.), 8.79 (s, 2, NH), 8.92 (s, 1, NH), 9.34 and 9.36 (d, 2, CH=N), 12.58 (d, 1, C=N'H+).

EXAMPLE 37

Disodium [9,10-anthracenediylbis [methylidyne-1-hydrazinyl-2-ylidene 4,5-dihydro-1H-imidazole-2,1-diyl)]]bis [phosphate]

To a stirred suspension of 585 mg of the compound prepared according to Example 6, [9,10-anthracenediylbis[methylidyne-1-hydrazinyl-2-ylidene (4,5-dihydro-1H-imidazole-2,1-diyl)]]bisphosphonic acid in 10 ml of water, monitored by a pH meter, was added dropwise 18.3 ml of 0.1N sodium hydroxide, at a rate such that the pH never exceeded 7.5 and gave a final pH of 7.4. This solution was evaporated at 35° C. over 5 hours, giving 629 mg of the desired product as an amorphous red-orange solid.

The compound prepared according to Example 37 was tested in the rat tail vein model for phlebitis reaction near the site of injection. For comparison purposes, a control placebo and bisantrene were also tested. The compounds were administered intravenously in an amount of 25 mg/kg. Observations were made at 1, 5 and 9 days following the injection.

No evidence of phlebitis was seen in the rat tail vein model that was administered the compound prepared according to Example 37, in contrast to bisantrene which did produce evidence of phlebitis near the site of injection.

EXAMPLE 38

[9,10-Anthracenediylbis[methylidyne-1-hydrazinyl-2-ylidene (4,5-dihydro-1H-imidazole-2,1-diyl)]]bisphosphonic Acid, Tetraethyl Ester (Alternate Method)

A suspension of 0.398 g of dried bis(2-imidazolin-2-ylhydrazone) of 9,10-anthracenedicarboxaldehyde in 5 ml of dimethylformamide was stirred for 5 hours with 0.359 g of diethyl cyanophosphate. The resulting very thick mixture was mixed with 15 ml of dry ether. The solid was collected and washed with ether to give 0.655 g of orange crystals, mp 215°-216° C. An infrared spectrum and results from thin layer chromatography (silica gel, CHCl$_3$—MeOH, 8/1 (v/v)) were the same as with the product of Example 4.

EXAMPLE 39

[6R-[6α, 7β(Z)]]-7-[[[2-[(Diethoxyphosphinyl)amino]-4-thiazolyl](methoxyimino)acetyl]amino]-8-oxo-5-thia-1-azabicyclo [4.2.0.]oct-2-ene-2-carboxylic Acid A solution of 5.40 mmol of ceftizoxime sodium salt (equivalent to 2 g of ceftizoxime) in 20 ml of water was acidified with 5.40 ml of 1N acetic acid. The resulting solid was collected and washed with ice water to give 1.90 g of ceftizoxime. A suspension of 1.85 g of ceftizoxime (dried at 80° C./0.1 mm) in 60 ml of methylene chloride was stirred overnight under argon with 2.03 g of N,O-bis(trimethylsilyl) acetamide and 1.73 g of diethyl chlorophosphate, whereupon the solid had dissolved. After a month the reaction mixture was evaporated to dryness and the residue was washed with water. The aqueous washes were extracted with chloroform, back-washing the chloroform extracts with water. Evaporation of the dried (MgSO$_4$) chloroform extracts left 0.049 g of a colorless gum; NMR (CDCl$_3$, 80 MHz) δ 1.37 (t, CH$_3$) δ 1.41 (t, CH$_3$), 4.17 (OCH$_2$, NOCH$_3$); IR (KBr) 1032 (P=O), 1787 (β-lactam).

EXAMPLE 40

1-Cyclopropyl-7-[4-(diethoxyphosphinyl)-1-piperazinyl]-6-fluoro-1,4-dihydro-4-oxo-3-quinolinecarboxylic Acid A suspension of 2.816 g (8.5 mmol) of ciprofloxacin base in 100 ml of dry CH$_2$Cl$_2$ was stirred under argon as 3.46 g (17 mmol) of N,O-bis(trimethylsilyl)acetamide was added. After the solid had dissolved (2-3 hours), 1.47 g (8.5 mmol) of diethyl chlorophosphate was added. After 24 hours at approximately 23° the solution was evaporated, finally at 0.03 mm for 15 hours. Washing of the solid residue with water gave a white solid which was dried and then recrystallized from CH$_2$Cl$_2$-toluene, boiling out the CH$_2$Cl$_2$ within 10 minutes to avoid thermal degradation. The product was 3.74 g (94%) of cream-colored solid, m.p. 192°-193° C.; NMR (CDCl$_3$, 80 MHz) δ 1.36 (t, CH$_3$), 3.30 (s, CH$_2$N), 4.06 (5 peaks, OCH$_2$); IR (KBr) 1028(P=O), 1630 (—COOH), 1724 cm$^{-1}$(C=O).

EXAMPLE 41

[(Phenylamino)[(4-phenyl-2-thiazolyl)amino]methylene]phosphoramidic Acid, Diethyl Ester A stirred suspension of 2.94 g (10 mmol) of 1-phenyl-3-(4-phenyl-2-thiazolyl) guanidine (dried at 110° C./0.1 mm) in 150 ml of methylene chloride was allowed to react with 2.03 g (10 mmol) of N,O-bis(trimethylsilyl) acetamide and 1.73 g (10 mmol) of diethyl chlorophosphate for 3 months by the procedure of Example 4. The reaction mixture was evaporated to dryness then was subjected to "dry column" chromatography (method of B. Loev and M. M. Goodman, Chem. and Industry, 2026 (1967) on 500 g of silica gel, and developed with 700 ml of methylene chloride-ethyl acetate, 9/1 (v/v). A band in the Nylon ® column at Rf 0.25-0.4, visualized as a dark band under ultraviolet light at 254 nm, was cut out, and extracted with chloroform-methanol, 3/1 (v/v). Evaporation of the extracts left 1.35 g of product as a pale yellow, thick syrup; NMR (CDCl$_3$, 80 MHz) δ 1.37 (t, 6H, CH$_3$), δ 4.11(5 peaks, 4H, OCH$_2$), 6.98 (s, 1H, =CH—S), 7.35(m, 10H, aromatic); IR (neat) 1653 (C=N) and 1032 cm$^{-1}$ (P=O); TLC (SiO$_2$, CHCl$_3$—MEOH, 19/1 (v/v)) showed only one spot under UV light.

EXAMPLE 42

Benz[cd]-indol-2-yl[2(1H-imidazol-1-yl)ethyl]phosphoramidic Acid

A solution of 2.61 g of N-[4-(1H-imidazol-1-yl)butyl]-benz[cd]-indol-2-amine in 65 ml of methylene chloride was allowed to react with 1.83 g of N,O-bis(trimethylsilyl)acetamide and 1.73 g of diethyl phosphoryl chloride for 1 month. The solution was filtered. The filtrate was chomatographed and the product was crystallized as in Example 4 to give 0.289 g of orange crystals, mp 157°-159° C.; NMR(CDCl$_3$, 80 MHz) δ 1.32 (t, 6H, CH$_3$), 1.83 (m, 4H, CH$_2$ CH$_2$CH$_2$CH$_2$), 3.99 (m, 8H, OCH$_2$, NCH$_2$), 6.87 (d, 2H, NCH=CHN), 7.27(m, 7H, aromatic and N—CH=N); IR (KBr) 1054 (P=O), 1675 cm$^{-1}$ (C=N).

Procedures analogous to that of Example 40 were used to prepare the phosphoramidic esters shown in Table IV of the following formula:

TABLE IV

| Example | Z | Yield, % | m.p., °C. |
|---|---|---|---|
| 43 | (CH$_3$O)$_2$P(=O)— | 94 | 217-220 |
| 44 | (C$_6$H$_5$O)$_2$P(=O)— | 98 | 145-150 (dec.)[a] |
| 45 | (1,3,2-dioxaphosphorinan-2-yl 2-oxide) | 96 | 246-249 (dec.) |
| 46 | (cyclohexyl-fused 1,3,2-dioxaphospholane 2-oxide) | 95 | 222 (dec.)[b] |

[a]Resolidified; remelted 190-193°.
[b]Began to sinter without melting. The recrystallization solvent was chloroform-methanol-toluene, boiling out solvent to b.p. 105°.

EXAMPLE 47

1-Cyclopropyl-6-fluoro-1,4-dihydro-4-oxo-7-(4-phosphono-1-piperazinyl)-3-quinolinecarboxylic Acid To a stirred solution of 2.34 g of the product of Example 40 in 25 ml of methylene chloride under argon was added 2.57 g of N,O-bis(trimethylsilyl)triflouroacetamide and then (after 10 minutes) 2.68 g of bromotrimethylsilane. After 17 hours, the solution was evaporated to dryness at 40° C./0.02 mm. The evaporation was then repeated twice after redissolving the residue in 25 ml portions of methylene chloride. A solution of the residual solid in 25 ml of methylene chloride was added to a stirred solution of 1 ml of water in 100 ml of acetone and then stirred for 15 minutes, to hydrolyze silyl ester groups. The resulting solid was collected and washed with acetone to give 2.24 g of cream-colored solid, m.p. 246°-252° (dec.); $^{31}$P-NMR (in DMSO with 5% triethylamine) δ 9.34 compared to δ 0.54 (at 50° C.) for a salt of ciprofloxacin with an equimolar amount of phosphoric acid, and δ 0.35 for phosphoric acid. The product was soluble in 0.1M phosphate buffer, pH 7.5, unlike ciprofloxacin.

EXAMPLE 48

1-Cyclopropyl-7-[4-diethoxyphosphinyl)-1-piperazinyl]-6-fluoro-1,4-dihydro-4-oxoquinolinecarboxylic Acid, Methyl Ester A dried (over KOH) solution of diazomethane in 3 ml of ether (prepared from 0.294 g of 1-methyl-3-nitro-1-nitrosoguanidine and 1 ml of 45% aqueous potassium hydroxide) was added to an ice-cold solution of 0.467 g of the product of Example 40 in 10 ml of methylene chloride. After two hours at 5° C., the solution was evaporated. A solution of the solid residue in 6 ml of acetone was filtered and evaporated to dryness. The residue crystallized from methylene chloride-n-butyl acetate as the methylene chloride was allowed to evaporate. Washing of the product with n-butyl acetate and with ether gave 0.339 g of a cream-colored solid, m.p. 192°-193° C.

EXAMPLE 49

1-Cyclopropyl-7-[4-(diethoxyphosphinyl)-1-piperazinyl]-6-fluoro-1,4-dihydro-4-oxo-3-quinolinecarboxylic Acid, 2-Methoxyethyl Ester To a solution of 0.467 g of the product of Example 40 in 5 ml of hexamethylphosphoramide was added 0.163 g of cesium carbonate, 0.304 g of 2-bromoethyl methyl ether, 0.137 g of 45% aqueous potassium hydroxide and 0.017 g of potassium iodide. The suspension was stirred in the dark under argon for 8 days. Ether (40 ml) was added and the mixture was extracted successively with water, brine and water. The ether layer was discarded. The aqueous layers were extracted with chloroform, the chloroform extracts were dried over sodium sulfate and then evaporated, finally at <100° and 0.06 mm. to remove hexamethylphosphoramide. Two recrystallizations of the solid residue from methylene chloride-n-heptane gave 0.424 g of ivory-colored needles, m.p. 138°-141° C. The product was easily soluble in water and in 0.1M phosphate buffer, pH 7.5.

EXAMPLE 50

1-Cyclopropyl-7-[4-diethoxyphosphinyl)-1-piperazinyl]-6-fluoro-1,4-dihydro-4-oxo-3-quinolinecarboxylic Acid, (Acetyloxy)methyl Ester Two decantations with n-heptane were used to wash the oil from 0.058 g of a 50% dispersion of NaH in mineral oil. A suspension of the hydride in 5 ml of N,N-dimethylacetamide containing 0.467 g of the product of Example 40 was stirred under argon for 10 minutes, when bubbling had almost stopped. The mixture was stirred and chilled with an ice bath during the dropwise addition of 0.275 g of bromomethyl acetate and for another 10 minutes. The mixture was stirred in the dark under argon without further cooling for 20 hours, following the extent of reaction by thin-layer chromatography with silica gel and $CHCl_3$—$CH_3OH$, 8/1, (v/v). The reaction mixture was gradually added to a vigorously stirred mixture of 5 g of ice, 5 ml of 5% aqueous $NaHCO_3$ and 10 ml of ethyl acetate. Stirring at <5° C. was continued for an hour to hydrolyze any unreacted bromo ester. The mixture was washed with brine, backwashing the brine with ethyl acetate. The combined, dried ($Na_2SO_4$) ethyl acetate solutions were evaporated. Recrystallization of the solid residue from $CH_2Cl_2$-n-heptane-ether and then from unheated $CH_2Cl_2$-diisopropyl ether, washing with ether, gave 0.462 g of ivory-colored solid, m.p. 168°-170° C.

Examples 51–58 were prepared analogously to example 50 to produce the phosphoramidic esters shown in Table V of the following formula:

TABLE V

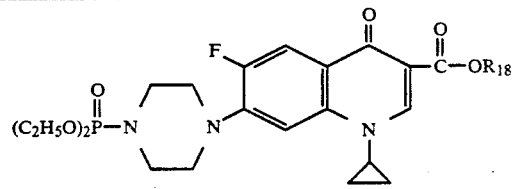

| Example | $R_{18}$ | Precursor | Reaction Time, Days | Yield % | M.P., °C. |
|---------|----------|-----------|---------------------|---------|-----------|
| 48 | $CH_3$ | See Full Example | See Ex. | 86 | 192–193 |
| 49 | $CH_3OCH_2CH_2$ | See Full Example | 5 | 81 | 138–141 |
| 50 | $CH_3CO$—$OCH_2$ | See Full Example | 1 | 86 | 168–170 |
| 51 | $C_2H_5$ | $C_2H_5I$ | 5 | 92 | 172–178[a] |
| 52 | $C_6H_5CH_2$ | $C_6H_5CH_2Br$ | 5 | 78 | 173–175[a] |
| 53 | ⟨cyclohexyl⟩$NCH_2CH_2$ | ⟨cyclohexyl⟩$NCH_2CH_2I$[b] | 7 | 7 | 133–136[c] |
| 54 | $CH_3CO$—$OCH(CH_3)$ | $CH_3CO$—$OCH(CH_3)Br$[d] | 10 | 31 | 147–150[a] |
| 55 | $(CH_3)_3C$—$CO$—$OCH_2$ | $(CH_3)_3C$—$CO$—$OCH_2I$[e] | 8 | 46 | 174–178[f] |
| 56 | $NCCH_2$ | $NCCH_2I$ | 15 | 25[g] | 186–187[f] |
| 57 | ⟨phthalide⟩ | ⟨phthalide-I⟩[e] | 2 | 41[g] | 140–144[f] |

TABLE V-continued

| | | | | | |
|---|---|---|---|---|---|
| 58 | HOCH$_2$CH$_2$ | HOCH$_2$CH$_2$Br | 21 | 44[h] | 172–175[f] |

[a]Recrystallizing by dissolving in CH$_2$Cl$_2$, treating with decolorizing charcoal, precipitating with n-hexane and washing with ether.
[b]The corresponding chloride.hydrochloride salt was stirred with 1.1 equivalents of NaI in acetone for 4 hours and evaporated to dryness. The residual solid and an extra equivalent of NaH were then condensed with the quinoline carboxylic acid. After 7 days, the unreacted acid was removed by pouring the reaction mixture into 1.0M sodium carbonate solution rather than using brine.
[c]A solution of the crude product in ethyl acetate was slowly evaporated to dryness with argon and the residual needles were washed with ether.
[d]L. Ulich and R. Adams, J. Am. Chem. Soc., 43, 660 (1921).
[e]The corresponding chloride was exchanged with 1.1 equivalents of NaI in acetone solution during 7.5 hours at about 24° C. in the dark, filtered, then added to the usual condensation mixture.
[f]A CH$_2$Cl$_2$ solution of the product crystallized when it was evaporated almost to dryness. The crystals were washed with ether.
[g]The crude, solid product was washed with 1N NH$_4$OH, then chromatographed on silica gel with CHCl$_3$—CH$_3$OH, 8/1 (v/v).
[h]The base used was 45% aqueous KOH instead of NaH. The reaction mixture (from 1 mmol of the starting quinoline carboxylic acid) was evaporated to dryness upon 2 g of Celite ® diatomaceous earth, then chromatographed on 32 g of neutral alumina with CH$_2$Cl$_2$—(CH$_3$)$_3$COH, 4:1 (v/v). Unreacted quinoline carboxylic acid remained at R$_f$0.0.

EXAMPLE 59

7-[5-(Diethoxyphosphinyl)-2,5-diazabicyclo[2.2.1]hept-2-yl]-1-(2,4-difluorophenyl)-6-fluoro-1,4-dihydro-4-oxo-3-quinolinecarboxylic Acid The method of Example 40 was used to phosphorylate 7-[2,5-diazabicyclo[2.2.1]-hept-2-yl]-1-(2,4-difluorophenyl)-6-fluoro-1,4-dihydro-4-oxo-3-quinolinecarboxylic acid (European Patent Application 251,308A). A solution of the water-washed, crude product in CH$_2$Cl$_2$ was dried over Na$_2$SO$_4$, filtered and then chromatographed on Bio-Sil A, eluting with a gradient of CH$_3$OH:CH$_2$Cl$_2$. The resulting white solid (21%) sintered and bubbled from 212°–216°.

EXAMPLE 60

[1,5-Pentanediylbis(oxy-4,1-phenylenecarbonimidoyl)-]bisphosphoramidic Acid, Tetraethyl Ester To a solution of 3 g of pentamidine diisethionate in 30 ml of water was gradually added with vigorous stirring 5.1 ml of 1M aqueous sodium carbonate. The resulting white solid, washed with 1N NH$_4$OH, amounted to 1.60 g of pentamidine base, m.p. 190°–191° C. (dec.). To a stirred suspension of 0.680 g of pentamidine base in 10 ml of dry dimethylformamide was added 0.652 g of diethyl cyanophosphonate. After 15 hours, the resulting solution was gradually diluted with 40 ml of water. The resulting solid was collected and washed with water to give 1.20 g of white needles, m.p. 149°–150° C.; NMR (300 MHz, CDCl$_3$) δ 1.34 (t, 12, CCH$_3$), 1.78 (m, 6, CH$_2$), 4.12 (m, 12, OCH$_2$), 6.13 (2, PNHC), 6.91 (m, 4, arom.), 7.81 (m, 4, arom.), 8.25 (2,=NH); IR (KBr) 1035 cm$^{-1}$ (P=O).

EXAMPLE 61

1,5-Pentanediylbis(oxy-4,1-phenylenecarbonimidoyl)]-bis-[phosphoramidic Acid], Compound with [(Ethylimino)-[4-[[5-[4-[imino(phosphonoamino) methyl]phenoxy]pentyl]oxy]phenyl]methyl]phosphoramidate (1:1), Monohydroiodide A solution of 0.306 g of the product of Example 60 in 5 ml CH$_2$Cl$_2$ was stirred under argon during addition of 0.500 g of iodotrimethylsilane. After 30 minutes in the dark, the solution was evaporated to dryness, finally at 23° C./0.03 mm. This evaporation was thrice repeated with 5 ml portions of CH$_2$Cl$_2$ to assure removal of excess silyl reagent and by-product C$_2$H$_5$I. Silyl ester functions in the residual solid were hydrolyzed by adding 5 ml of acetone and 0.018 ml of water without stirring. After an hour, the supernatant solution was discarded and replaced by 5 ml of CH$_2$Cl$_2$ whereupon the gel-like product solidified. The solid was pulverized in the CH$_2$Cl$_2$ and a solution of 0.018 ml of water in 5 ml of acetone was added without agitation. Thus, although the solid became gummy, it remained porous to allow completion of hydrolysis. After 30 minutes, the product had hardened. Collection by filtration and washing with acetone and with CH$_2$Cl$_2$ gave 0.289 g of yellow-tan solid. It sintered from 160° C.; gas evolved from 220° C.; MS(+FAB) 501(M+H), 529(M$^1$+H=MC$_2$H$_5$); IR (KBr) 1048 and 1081 cm$^{-1}$ (P=O).

EXAMPLE 62

(Z)-2-[(Diethoxyphosphinyl)amino-α-(methoxyimino)-4-thiazoleacetic Acid, Ethyl Ester To a stirred solution of 4.6 g (0.02 mol) of ethyl 2-(aminothiazol-4-yl)-Z-2-methoxyiminoacetate in 40 ml pyridine at 10°–20° was added 9.0 ml (0.6 mol) diethyl chlorophosphate. The solution was stirred at room temperature for 2 hours. Pyridine was evaporated and the residue was codistilled with benzene and partitioned between water and methylene chloride. The methylene chloride layer was washed with excess 10% aqueous HCl, water, aqueous bicarbonate, saturated sodium chloride, and dried over sodium sulfate. Upon evaporation, 5.5 g brown oil was obtained which was purified on Biosil A using hexane/ethyl acetate (1:4) to afford 2.8 g of yellow crystals, m.p. 96.5–98.0; NMR (300MH$_2$, DCCl$_3$) δ 1.35 (3t, 9, CH$_2$CH$_3$), 3.97 (S, 3, OCH$_3$), 4.17 (q, 4, OCH$_2$), 4.39 (q, 2, OCH$_2$), 6.93 (s, 1, thiazole H).

EXAMPLE 63

(Z)-2-[(Diethoxyphosphinyl)amino]-α-(methoxyimino)-4-thiazoleacetic Acid

A solution of 8.4 g (0.023 mol) (Z)-2-[(diethoxyphosphinyl)amino]-α-(methoxyimino)-4-thiazoleacetic acid, ethyl ester, 9.25 ml (0.046 mol) 5N sodium hydroxide, 30 ml water, and 50 ml dioxane was stirred at room temperature for 18 hours. The solvent was evaporated, 30 ml of 50% saturated sodium chloride was added, the pH was adjusted to 4.5, and 3×30 ml ethyl acetate was added. The aqueous layer was then adjusted to pH 2.5, and extraction with ethyl acetate followed by evaporation yielded 4.6 g of a yellow oil; MS ((+) FAB), 338 (M+H); NMR (300 MHz, DCCl$_3$) δ 1.36 (2t, 6, OCH$_2$CH$_3$), 4.01 (s, 3, OCH$_3$), 4.18 (m, 4, OCH$_2$), 7.10 (s, 1, thiazole H).

EXAMPLE 64

6R-[6-α, 7-β(Z)]]-3-[(Acetyloxy)methyl]-7-[[[2-[(diethoxyphosphinyl)amino]-4-thiazolyl](methoxyimino)acetyl]amino]-8-oxo-5-thia-1-azabicyclo [4.2.0]oct-2-ene-2-carboxylic Acid, Diphenylmethyl Ester A solution of 1.69 g (5 mmol) of (Z)-2-[(diethoxyphosphinyl)amino]-α-(methoxyimino)-4-thiazoleacetic acid, 0.75 g (5 mmol) of 1-hydroxybonzotriazole hydrate, and 1.03 g (5 mmol) dicyclohexylcarbodiimide in 30 ml methylene chloride was stirred at room temperature for 2 hours and filtered. To the filtrate was added 2.19 g (5 mmol) 7-aminocephalosporanic acid ("7-ACA"), benzhydryl ester, and stirring was continued overnight at room temperature. The mixture was filtered, washed with water and saturated sodium chloride, dried over sodium sulfate, and evaporated. The residue was chromotographed on Biosil A using methylene chloride plus 1% methanol to give 1.68 g of the desired product; MS ((+) FAB), 758 (M+H); IR (KBr, cm$^{-1}$) 1790, 1734; NMR (300 MHz, d$_6$-DMSO) δ 1.25 (2t, 6, OCH$_2$CH$_3$), 1.96 (s, 3, CH$_3$C=O), 3.62 (pair of doublets, 2, endocyclic-CH$_2$S—), 3.88 (s, 3, OCH$_3$), 4.05 (m, 4, OCH$_2$), (AB quartet, 2, exocyclic-CH$_2$S—), 5.23 (d, 1, 6H of 7-ACA), 5.92 (dd, 1, 7H of 7-ACA), 6.29 (s, 1, thiazole H), 7.15–7.70 (m, 11, CHQ$_2$), 9.72 (d, 1H, NH).

EXAMPLE 65

[6R-[6-α, 7-β(Z)]]-3-[(Acetyloxy)methyl]-7-[[[2-[(diethylphosphinyl)amino]-4-thiazolyl](methoxyimino)acetyl]amino1-8-oxo-5-thia-1-azabicyclo[4.2.0]oct-2-ene-2-carboxylic Acid 1.0 g of [6R-[6-α, 7-β(Z)]]-3-[(acetyloxy)methyl]-7-[[[2-[(diethoxyphosphinyl)amino]-4-thiazolyl](methoxyimino)acetyl]amino]-8-oxo-5-thia-1-azabicyclo[4.2.0]oct-2-ene-2-carboxylic acid, diphenylmethyl ester was stirred at room temperature in 15 ml trifluoroacetic acid with 1.0 ml anisole. Trifluoroacetic acid was evaporated and the residue was stirred with methylene chloride and saturated aqueous sodium bicarbonate. The aqueous layer was adjusted to pH 2 and extracted with methylene chloride. This organic layer was washed with water and saturated sodium chloride, dried over sodium sulfate and evaporated to yield 0.5 g of a yellow solid; MS ((+) FAB), 592 (M+H); IR (KBr, cm$^{-1}$) 1786, 1734; NMR (300 MHz, d$_6$-DMSO) δ 1.34 (t, 6, OCH$_2$CH$_3$), δ 2.08 (s, 3, CH$_3$C=O), 3.49 (pair of doublets, 2, endocyclic-CH$_2$S—), 4.03 (s, 3, OCH$_3$), 4.15 (m, 4, CH$_2$OP=O), 5.00 (m, 2, exocyclic—CH$_2$S—), 5.18 (d, 1, 6H of 7-ACA), 5.89 (dd, 1, 7H-of 7-ACA), 7.21 (s, 1, thiazole H), 8.05 (d, 1H, NH).

EXAMPLE 66

[6R-[6-α, 7-β(Z)]]-3-(Chloromethyl)-7-[[[2-[(diethoxyphosphinyl)amino]-4-thiazolyl](methoxyimino)acetyl]amino]-8-oxo-5-thia-1-azabicyclo[4.2.0]oct-2-ene-2-carboxylic Acid (4-methoxyphenyl)methyl Ester The procedure of example 64 was repeated using 2.63 g (6.5 mmol) 7-amino-3-chloromethylceph-3-em-4-carboxylic acid, 2,2 g (6.5 mmol) (Z)-2-[(diethoxyphosphinyl)amino]-α-(methoxyimino)-4-thiazoleacetic acid, 1.05 g (6.5 mmol) 1-hydroxybenzotriazole hydrate, and 2,2 g (11 mmol) dicyclohexylcarbodiimide to yield 2.25 g of the desired product; MS ((+) FAB), 688 (M+H).

EXAMPLE 67

[6R-[6-α, 7-β(Z)]]-7-[[[2-[(Diethoxyphosphinyl)amino]-4-thiazolyl]-(methoxyimino) acetyl]amino]-8-oxo-3-[(1,2,3-thiadiazol-5-ylthio)methyl]-5-thia-1-azabicyclo[4.2.0]oct-2-ene -2-carboxylic acid (4-methoxyphenyl)methyl Ester

[6R-[6-α, 7-β(Z)]]-3-(chloromethyl)-7-[[[2-[(diethoxyphosphinyl)amino]-4-thiazolyl]-(methoxyimino)acetyl]amino]-8-oxo-5-thia-1-azabicyclo[4.2.0]oct-2-ene-2-carboxylic acid, (4-methoxyphenyl)methyl ester (0.8 g) and 0.4 g sodium 5-mercapto-1,2,3-thiadiazole were stirred in 30 ml acetone plus 15 ml water for 30 minutes. The solvent was evaporated to dryness and the residue was columned on Biosil A using methylene chloride containing 0.5 to 1.0% methanol to give 687 mg of product; MS ((+)FAB) 770 (M+H); IR (KBr,cm$^{-1}$) 1786, 1720.

EXAMPLE 68

[6R-[6-α, 7-β(Z)]]-7-[[[2-[(Diethoxyphosphinyl)amino]-4-thiazolyl]-(methoxyimino) acetyl]amino]-8-oxo-3-[(1,2,3-thiadiazol-5-ylthio)methyl]-5-thia-1-azabicyclo[4.2.0]oct-2-ene -2-carboxylic acid

[6R-[6-α, 7-β(Z)]]-7-[[[2-[(diethoxyphosphinyl)amino]-4-thiazolyl]-(methoxyimino)acetyl]amino]-8-oxo-3-[(1,2,3-thiadiazol-5-ylthio)methyl]-5-thia-1-azabicyclo [4.2.0]oct-2-ene-2-carboxylic acid (4-methoxyphenyl)methyl ester (90 mg) was added to a stirred solution of 2 ml trifluoroacetic acid and evaporated without heating. The residue was washed with ether several times and dissolved in aqueous sodium bicarbonate. The aqueous layer was washed with methylene chloride, acidified to pH 3, and extracted again with methylene chloride. The methylene chloride fraction was dried over Na$_2$SO$_4$ and evaporated to give 41 mg of a white solid; MS ((+) FAB), 650 (M+H); IR (KBr, cm$^{-1}$) 1782; NMR (300MHz, d$_6$-DMSO) δ 1.38 (t, 6, OCH$_2$CH$_3$), 3.75 (m, 2, endocyclic-CH$_2$S—), 4.07 (s, 3, OCH$_3$), 4.18 (m, 6, exocyclic-CH$_2$S & OCH$_2$), 5.06 (d, 1H, 6H of 7-ACA), 5.81 (dd, 1, 7H of 7-ACA), 7.24 (s, 1, thiazole H), 8.51 (s, 1, thiadiazole H).

EXAMPLE 69

[6R-[6-α, 7-β(Z)]]-7-[[[2-[(Diethoxyphosphinyl)amino]-4-thiazolyl]-(methoxyimino)acetyl]amino]-3-[[(1-methyl-1H-tetrazol-5-yl) thio]methyl]-8-oxo-5 thia-1-azabicyclo[4.2.0]oct-2-ene2-carboxylic Acid, (4-methoxyphenyl)methyl Ester The procedure of example 67 was repeated using 417 mg of [6R-[6-α, 7-β(Z)]]-3-(chloromethyl)-7-[[[2-[(diethoxyphosphinyl) amino]-4-thiazolyl]-(methoxyimino)acetyl]amino]-8-oxo-5-thia-1-azabicyclo[4.2.0]oct-2-ene-2-carboxylic acid, (4-methoxyphenyl)methyl ester and 140 mg sodium 5-mercapto-1-methyltetrazole hydrate in 3 ml methanol to afford 410 mg of the desired product; MS ((+)FAB), 768 (M+H).

EXAMPLE 70

[6R-[6-α, 7-β(Z)]]-7-[[[2-[(Diethoxyphosphinyl)amino-4-thiazolyl]-(methoxyimino)acetyl]amino]-3-[[(1-methyl-1H-tetrazol-5-yl)thio]methyl]-8-oxo-5 thia-1-azabicyclo[4.2.0]oct-2-ene2-carboxylic Acid, The procedure of example 68 was repeated using 350 mg of [6R-[6-α, 7-β(Z)]]-7-[[[2-[(diethoxyphosphinyl)amino]-4-thiazolyl]-(methoxyimino)acetyl]amino]-3-[[(1-methyl-1H-tetrazol-5-yl)thio]methyl]-8-oxo-5-thia-1-azabicyclo [4.2.0]oct-2-ene-2-carboxylic acid, (4-methoxyphenyl)methyl ester and 0.075 ml anisole in trifluoroacetic acid for 5 minutes. The product was obtained by acidification in aqueous bicarbonate and extraction with methylene chloride in the pH range 3.2 to 3.0 to give 200 mg of the desired product; MS ((+) FAB), 648 (M+H); NMR (300 MHz, $d_6$-DMSO) δ 1.28 (t, 6, OCH$_2$CH$_3$), 3.71 (pair of doublets, 2, endocyclic-CH$_2$S—), 3.85 (s, 3, NCH$_3$), 3.97 (s, 3, OCH$_3$), 4.07 (m, 4, CH$_2$OP=O), 4.33 (m, 2, exocyclic-CH$_2$S—) 5.01 (d, 1, 6H of 7-ACA), 5.79 (dd, 1, of 7-ACA), 7.19 (d, 1, NH).

We claim:

1. A compound of the formula

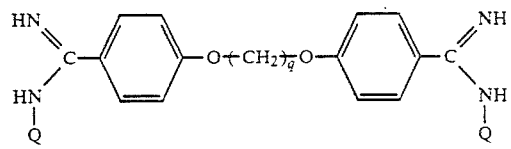

wherein
q is an integer from 1 to 7, Q is hydrogen or A, wherein A is

such that R' and R" may be the same or different and (where R is $C_1$-$C_6$ alkyl, $C_6H_5$—, $C_6H_5$—CH$_2$—, NC—CH$_2$CH$_2$—,

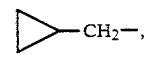

Cl$_3$C—CH$_2$— or R$_7$OCH$_2$CH$_2$—, where R$_7$ is hydrogen or $C_1$-$C_6$ alkyl), hydrogen, or a pharmaceutically acceptable cation or R' and R" are linked to form a —CH$_2$—CH$_2$ or a

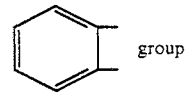 group provided that at least one Q is A.

2. The compound of claim 1 wherein q=5.
3. The compound of claim 1 wherein one of R' and R" is hydrogen and the other is a pharmacologically acceptable cation.
4. The compound according to claim 1, wherein said pharmaceutically acceptable cation is sodium, potassium, or ammonium.
5. A pharmaceutical composition of matter comprising an effective amount of a pro-drug compound of claim 1 in association with a pharmaceutically acceptable carrier.
6. The compound according to claim 1, [1,5-Pentanediylbis(oxy-4,1-phenylenecarbonimidoyl)]-bisphosphoramidic Acid, Tetraethyl Ester.
7. The compound according to claim 1, [1,5-Pentanediylbis(oxy-4,1-phenylenecarbonimidoyl)]-bis[-phosphoramidic Acid].

* * * * *

IN THE UNITED STATES PATENT AND TRADEMARK OFFICE

CERTIFICATE OF CORRECTION

PATENT NUMBER: 5,070,082

DATED: December 3, 1991

INVENTOR(S): Keith C. Murdock, Ving J. Lee

It is certified that error appears in the above-identified patent and that said Letters Patent is hereby corrected as shown below:

In column 42, line 19, after "and" insert -- are R --.

Signed and Sealed this

Sixth Day of April, 1993

Attest:

STEPHEN G. KUNIN

Attesting Officer

Acting Commissioner of Patents and Trademarks